United States Patent
Combs et al.

(10) Patent No.: US 7,071,333 B2
(45) Date of Patent: Jul. 4, 2006

(54) TRIAZOLOPURINE-BASED TRICYCLIC COMPOUNDS AND PHARMACEUTICAL COMPOSITIONS COMPRISING SAME

(75) Inventors: Donald Combs, Neptune City, NJ (US); Charles M. Langevine, Brooklyn, NY (US); Yuping Qiu, Glastonbury, CT (US); Fred Christopher Zusi, Hamden, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/901,677

(22) Filed: Jul. 29, 2004

(65) Prior Publication Data

US 2005/0038054 A1    Feb. 17, 2005

Related U.S. Application Data

(60) Provisional application No. 60/491,170, filed on Jul. 30, 2003.

(51) Int. Cl.
- C07D 487/14 (2006.01)
- A61K 31/519 (2006.01)
- A61P 11/06 (2006.01)
- A61P 19/02 (2006.01)

(52) U.S. Cl. .................. 544/251; 514/267
(58) Field of Classification Search ............... 514/267; 544/251
See application file for complete search history.

(56) References Cited

U.S. PATENT DOCUMENTS 6,492,377 B1    12/2002    Blech et al.

FOREIGN PATENT DOCUMENTS

| WO | WO 98/03511 | 1/1998 |
|---|---|---|
| WO | WO 99/65912 | 12/1999 |
| WO | WO 00012511 | 3/2000 |
| WO | WO 00/35428 | 6/2000 |
| WO | WO 02/069945 | 9/2002 |
| WO | WO 03/105902 | 12/2003 |
| WO | WO 2004/004704 | 1/2004 |

OTHER PUBLICATIONS

West, Anthony R., Solid State Chemistry and its Applications, Wiley, New York, 1988, pp. 358 &365.*
Draetta, G. and Pagano, M. in "Annual Reports in Medicinal Chemistry, vol. 31", 1996, Academic Press, San Diego, p. 241-246.*
Chantry, D., Emerging Drugs, 1999, Chapter 1, pp. 5-13.*
Gabor G Illei, and Peter E Lipsky, Current Opinion in Immunology vol. 12, Issue 6, Dec. 1, 2000, pp. 712-718.*
Black, Roy A. et al, Ann. Rep. Med. Chem., 32, 1997, 241-250.*
Tenor et al., "1,2,4-Triazoles. VII. Synthesis and Reactivity of 7-amino-s-triazolo[1,5-a]-5-pyrimidones", Univ. Greifswald, Germany, *Ber.*, vol. 97(5), pp. 1373-1382, 1964. (*Eng. Abstract*).

* cited by examiner

*Primary Examiner*—Thomas C. McKenzie
(74) *Attorney, Agent, or Firm*—Mary VanAtten

(57) ABSTRACT

The present invention provides for triazolopurine-based tricyclic compounds having the formula (I),

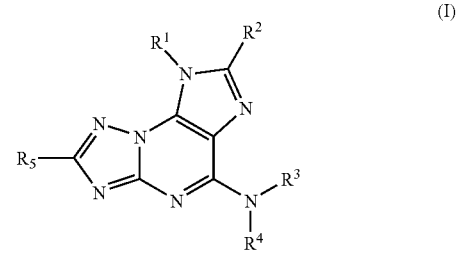

wherein $R^1$, $R^2$, $R^3$, $R^4$, and $R^5$ are as described herein. The present invention further provides pharmaceutical compositions comprising such compounds, as well as the use of such compounds for treating inflammatory and immune diseases.

10 Claims, No Drawings

TRIAZOLOPURINE-BASED TRICYCLIC COMPOUNDS AND PHARMACEUTICAL COMPOSITIONS COMPRISING SAME

CROSS-REFERENCE TO RELATED APPLICATIONS

The present application claims the priority benefit of U.S. Provisional Application No. 60/491,170, filed Jul. 30, 2003, which is expressly incorporated fully herein by reference.

FIELD OF THE INVENTION

The present invention relates to triazolopurine-based tricyclic compounds, to methods of using the compounds in treating inflammatory and immune diseases, and to pharmaceutical compositions comprising same.

BACKGROUND OF THE INVENTION

Tumor necrosis factor (TNF-α) is a potent cytokine having pro-inflammatory properties that is released by many cell types when stimulated. Studies have shown a relationship between elevated levels of TNF-α and a variety of diseases such as septic shock, hematopoiesis, tumors, and inflammatory disorders of the central nervous system, including HIV encephalitis, cerebral malaria, and meningitis. More recently agents which inhibit the action of TNF-α have demonstrated clinical utility in a variety of diseases such as rheumatoid arthritis, psoriasis, and inflammatory bowel disease. Additionally Certain neurodegenerative diseases such as Alzheimer's disease, Parkinson's disease, and Creutzfeldt-Jacob disease also are reportedly associated with enhanced TNF-α levels. See, e.g., Arvin et al., "*The Role of Inflammation and Cytokines in Brain Injury,*" *Neuroscience and Biobehavioral Reviews*, Vol. 20, No. 3 (1996), at pp. 445–452.

Accordingly, various classes of drugs have been researched and developed to inhibit TNF-α production at both transcriptional and translational levels, e.g., corticosteroids, rolipram (a phosphodiesterase IV inhibitor suppressing TNF-α mRNA synthesis), calphostin, and imidazole-type cytokine suppressing anti-inflammatory drugs (CSAIDs). These drugs are useful in treating a variety of diseases. See Dinarello, "*Role of Pro- and Anti-Inflammatory Cytokines During Inflammation: Experimental and Clinical Findings, Review*, Vol. 0393-974X (1997), at pp. 91–103.

Recently, attention has focussed on the role of Nuclear factor κB (NF-κB) in the activation pathway that leads to production of TNF-α and other inflammatory cytokines and gene products. Besides TNF-α, NF-κB is involved in the regulation of a variety of genes involved in immune function and inflammation. These include the cytokines IL-1, IL-2, IL-6, IL-2Rα, and GM-GSF, the chemokines IL-8, MCP-1 (CCR2), and RANTES, the adhesion molecules, intercellular adhesion molecule-1 (ICAM-1), vascular cellular adhesion molecule-1 (VCAM-1) and E-selectin, the proteases matrix metalloproteinase-1 (MMP-1), MMP-9 and MMP-13, and the pro-inflammatory enzymes cyclooxygenase-2 (COX-2), iNOS, and cPLA$_2$. Thus, inhibition of NF-κB and/or its activation pathway provides a means for treating various diseases including autoimmune diseases, inflammatory diseases, Alzheimer's disease, atherosclerosis, oncogenesis, and so forth by a variety of modes of action (i.e. cytokine reduction, chemokine reduction, reduction of adhesion molecule, decreased expression of certain proteases implicated in inflammatory and immune disease processes, and decreased production of enzymes which produce pro-inflammatory mediators) which have been implicated in a variety of disease progression. See, e.g., Baldwin, "*The NF-κB and IκB Proteins: New Discoveries and Insights,*" *Annual Rev. Immunol.*, Vol. 14 (1996), at pp. 649–81; see also Christman et al., "*Impact of Basic Research on Tomorrow's Medicine, The Role of Nuclear Factor-κB in Pulmonary Diseases,*" *Chest*, Vol. 117 (2000), at pp. 1482–87, and Roshak, et al., "*Small-molecule Inhibitors of NF-κB for the Treatment of Inflammatory Joint Disease.*" *Current Opinion in Pharmacol.* Vol. 2 (2002) pp. 316–321.

IκB is a cytoplasmic protein that controls NF-κB activity by retaining NF-κB in the cytoplasm. IκB is phosphorylated by the IκB kinase (IKK), which has two isoforms, IKK-α ("IKK-1") and IKK-β ("IKK-2"). When IKK phosphorylates IκB, NF-κB is rapidly released from the cytoplasm into the cell. Upon release into the cell, NF-κB translocates to the nucleus where it binds to the promoters of many genes and up-regulates the transcription of pro-inflammatory genes. Thus inhibitors of IKK-1 and/or IKK-2 would prevent translocation of NF-κB to the nucleus and prevent transcription of the pro-inflammatory gene products described above. For example see Burke, et al. "*BMS-345541 is a Highly Selective Inhibitor of IκB Kinase that Binds at an Allosteric Site of the Enzyme and Blocks NF-κB dependent Transcription in Mice.*" *J. Biol. Chem.* Vol. 278, (2003) pp. 1450–1456.

The therapeutic effects of glucocorticoids are mediated in part by their ability to inhibit NF-κB activity by two mechanisms, i.e., up-regulating IκB protein levels and inhibiting NF-κB subunits. The deleterious side effects of glucocorticoids (such as osteoporosis, hyperglycemia, fat redistribution, etc.) have been postulated to result from the interaction of glucocorticoids with the glucocorticoid receptor (GR) or the glucocorticoid response element (GRE). For example see Schacke, et al. "*Mechanisms Involved in the Side Effects of Glucocorticoids*" *Pharmacol. and Therapeutics* Vol 96 (2002) pp. 23–43. Thus inhibitors of IKK-1 and/or IKK-2 inhibitors should provide much of the therapeutic benefit of glucocorticoids with a greatly improved side effect profile.

As may be appreciated, those in the field of pharmaceutical research continue to seek to develop new compounds and compositions having increased effectiveness, bioavailability, and solubility, having fewer side effects, and/or providing the physician and consumer with a choice of options. Particularly in the area of immune response, many individuals respond differently depending upon the type of treatment and chemical agent used. Mechanisms of action continue to be studied to aid in understanding the immune response and in developing compounds effective for treating inflammatory and immune-related disorders.

The present invention provides triazolopurine-based tricyclic compounds useful as inhibitors of IKK.

SUMMARY OF THE INVENTION

The invention is directed to compounds of formula (I), useful in treating inflammatory or immune conditions:

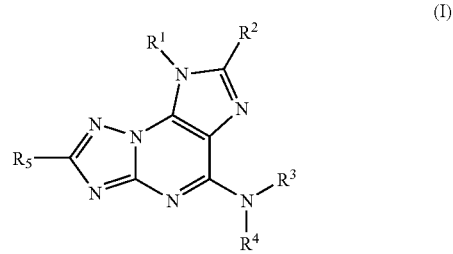

(I)

enantiomers, diastereomers, salts, and solvates thereof.

The invention also relates to pharmaceutical compositions containing at least one compound of formula (I) and a pharmaceutically-acceptable carrier or diluent, for use in treating inflammatory and immune diseases. Also included within the invention are methods of treating such diseases comprising administering to a mammal in need of such treatment an effective amount of at least one compound of formula (I).

The invention also relates to novel compounds for use in therapy.

The present invention also relates to the use of novel cyclic derivatives for the manufacture of a medicament for the treatment of inflammatory diseases.

DETAILED DESCRIPTION OF EMBODIMENTS OF THE INVENTION

[1] In one embodiment, the present invention is directed to a compound of formula (I),

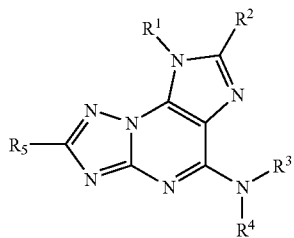

(I)

enantiomers, diastereomers, salts, and solvates thereof wherein $R^1$ is
(a) hydrogen, or
(b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^1$, $Z^2$ and $Z^3$;
(c) —$OR^{9a}$;

$R^2$ is
(a) hydrogen, halo, cyano,
(b) alkyl, alkenyl, alkynyl, haloalkyl, alkoxy, cycloalkoxy, heterocyclooxy, aryloxy, heteroaryloxy, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1a}$, $Z^{2a}$ and $Z^{3a}$; or
(c) —$OR^{9a}$, —$SR^{9a}$ or —$SO_2R^{9a}$ $R^3$ and $R^4$ are independently
(a) hydrogen,
(b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1b}$, $Z^{2b}$ and $Z^{3b}$;
(c) —$OR^{10}$, —$NR^{11}R^{12}$, —$N(R^{11})C(O)R^{10}$, —$N(R^{11})C(O)OR^{12}$, —$N(R^{11})SO_2R^{13}$, or —$C(O)NR^{11}R^{12}$, —$SO_2NR^{11}R^{12}$, —$N(R^{11})C(O)NR^{11a}R^{12}$, or —$N(R^{11})SO_2NR^{11a}R^{12}$; or
(d) $R^3$ and $R^4$ together with the nitrogen atom to which they are attached combine to form a heterocyclo ring optionally independently substituted as valence allows with one or more $Z^{1b}$, $Z^{2b}$ and $Z^{3b}$;

$R^5$ is
(a) hydrogen, hydroxy, halo, or cyano,
(b) alkyl, alkenyl, alkynyl, cycloalkyl, heterocyclo, aryl, heteroaryl, (cycloalkyl)alkyl, (heterocyclo)alkyl, (aryl)alkyl, or (heteroaryl)alkyl any of which may be optionally independently substituted as valence allows with one or more $Z^{1d}$, $Z^{2d}$ and $Z^{3d}$; or
(c) —$R^{6a}$, —$SR^{9a}$, $SO_2R^{9a}$, $SO_2NR^{7a}R^{8a}$, $NR^{7a}R^{8a}$, $N(R^{7a})SO_2R^9$, —$N(R^{7a})SO_2NR^{7b}R^{8b}$, —$N(R^{7a})C(O)R^{6a}$, $N(R^{7a})C(O)NR^{7b}R^{8b}$, —$N(R^{7a})C(O)OR^{6a}$, —$C(O)R^{6a}$, —$C(O)OR^{6a}$, —$OC(O)R^{6a}$, —$C(O)NR^{7a}R^{8a}$, or —$OC(O)NR^{7a}R^{8a}$;

$R^{6a}$ and $R^{6b}$ are independently
(a) hydrogen, or
(b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1c}$, $Z^{2c}$ and $Z^{3c}$;

$R^{7a}$, $R^{7b}$, $R^{8a}$ and $R^{8b}$ are independently
(a) hydrogen,
(b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1d}$, $Z^{2d}$ and $Z^{3d}$; or
(c) —$OR^{6b}$, —$NR^7CR^{8c}$, —$N(R^{7c})SO_2R^{9b}$, —$N(R^{7c})C(O)R^{6b}$, —$N(R^{7c})C(O)OR^{6b}$, —$SO_2NR^7CR^{8c}$, —$S_2R^{9b}$, —$C(O)R^{6b}$, —$C(O)OR^{6b}$, or $C(O)NR^7CR^{8c}$;
(d) $R^{7a}$ and $R^{8a}$ together with the nitrogen atom to which they are attached combine to form a heterocyclo ring optionally independently substituted as valence allows with one or more $Z^{1d}$, $Z^{2d}$ and $Z^{3d}$;

$R^{7c}$ and $R^{8c}$ are independently
(a) hydrogen,
(b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1d}$, $Z^{2d}$ and $Z^{3d}$;
(c) $R^{7c}$ and $R^{8c}$ together with the nitrogen atom to which they are attached combine to form a heterocyclo ring optionally independently substituted as valence allows with one or more $Z^{1d}$, $Z^{2d}$ and $Z^{3d}$;

$R^9$, $R^{9a}$ and $R^{9b}$ are independently alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1d}$, $Z^{2d}$ and $Z^{3d}$;

$R^{10}$, $R^{11}$, $R^{11a}$ and $R^{12}$ are independently
(a) hydrogen, or
(b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1e}$, $Z^{2e}$ and $Z^{3e}$;
(c) $R^{11}$ and $R^{12}$ together with the nitrogen atom to which they are attached combine to form a heterocyclo ring optionally independently substituted as valence allows with one or more $Z^{1d}$, $Z^{2d}$ and $Z^{3d}$;

$R^{13}$ is alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1e}$, $Z^{2e}$ and $Z^{3e}$;

$Z^{1-1^e}$, $Z^{2-2^e}$, and $Z^{3-3^e}$ are optional substituents at each occurrence independently selected from $W^{1-5}$ optionally substituted as valance allows with $V^{1-5}$;

where $W^{1-5}$ are independently
(1) a bond
(2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl; or where $V^{1-5}$ are independently
(1) H
(2) alkyl, haloalkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl;
(3) —$U^1$—O—$Y^5$,
(4) —$U^1$—S—$Y^5$,
(5) —$U^1$—(O)$_r$—H, —$U^1$—C(O)$_t$—$Y^5$ where t is 1 or 2,
(6) —$U^1$—SO$_3$—H, or —$U^1$—S(O)$_t$$Y^5$,
(7) —$U^1$-halo,
(8) —$U^1$-cyano,
(9) —$U^1$-nitro,
(10) —$U^1$—N$Y^2Y^3$,
(11) —$U^1$—N($Y^4$)—C(O)—$Y^1$,
(12) —$U^1$—N($Y^4$)—C(S)—$Y^1$,
(13) —$U^1$—N($Y^4$)—C(O)—N$Y^2Y^3$,
(14) —$U^1$—N($Y^4$)—C(S)—N$Y^2Y^3$,
(15) —$U^1$—N($Y^4$)—C(O)O—$Y^5$,
(16) —$U^1$—N($Y^4$)$_n$—S(O)$_2$—$Y^1$,
(17) —$U^1$—N($Y^4$)—S(O)$_2$—N$Y^2Y^3$,
(18) —$U^1$—C(O)—N$Y^2Y^3$,
(19) —$U^1$—OC(O)—N$Y^2Y^3$,
(20) —$U^1$—S(O)$_2$—N($Y^4$)—$Y^1$,
(21) —$U^1$—N($Y^4$)—C(=N$V^{1^a}$)—N$Y^2Y^3$,
(22) —$U^1$—N($Y^4$)—C(=N$V^{1^a}$)—$Y^1$,
(23) —$U^1$—C(=N$V^{1^a}$)—N$Y^2Y^3$,
(24) oxo;
(25) $Y^5$;
(26) —$U^1$—C(O)—N$Y^2$—O$Y^5$, $V^{1^a}$ is independently hydrogen, alkyl, —CN, —C(O)$Y^1$, —S(O)$_2Y^5$, S(O)$_2$N$Y^2Y^3$; $Y^1$, $Y^2$, $Y^3$, $Y^4$ and $Y^5$
(1) are each independently hydrogen, alkyl, haloalkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco) alkyl, heteroaryl, or (heteroaryl)alkyl; or
(2) $Y^2$ and $Y^3$ may together be alkylene or alkenylene, completing a 3- to 8-membered saturated or unsaturated ring together with the atoms to which they are attached, or
(3) $Y^2$ or $Y^3$, together with $Y^1$, may be alkylene or alkenylene completing a 3- to 8-membered saturated or unsaturated ring together with the nitrogen atoms to which they are attached, or
(4) $Y^2$ and $Y^3$ together with the nitrogen atom to which they are attached may combine to form a group —N=C$Y^6Y^7$ where $Y^6$ and $Y^7$ are each independently H or alkyl; and $U^1$ is independently
(1) a single bond,
(2) alkylene,
(3) alkenylene,
(4) alkynylene,
(5) —$U^2$—O—$U^3$—,
(6) —$U^2$—N$Y^4$—$U^3$—,
(7) —$U^2$—S—$U^3$—, or
(8) —$U^2$—S(O)$_2$—$U^3$—, $U^2$ is independently selected from
(1) a single bond,
(2) alkylene,
(3) alkenylene,
(4) alkynylene; and $U^3$ is independently selected from
(1) alkylene,
(2) alkenylene,
(3) alkynylene.

[2] In another embodiment, the present invention is directed to a compound of Formula (I) wherein
$R^3$ and $R^4$ are independently
(a) hydrogen,
(b) alkyl, haloalkyl, (hydroxy)alkyl, cycloalkyl, (cycloalkyl)alkyl, (heterocyclo)alkyl, (aryl)alkyl or (heteroaryl)alkyl and of which may be optionally independently substituted as valence allows with one or more $Z^{1^b}$, $Z^{2^b}$ and $Z^{3^b}$; or
(c) $R^3$ and $R^4$ together with the nitrogen atom to which they are attached combine to form a heterocyclo ring optionally independently substituted as valence allows with one or more $Z^{1^b}$, $Z^{2^b}$ and $Z^{3^b}$.

[3] In another embodiment, the present invention is directed to a compound of Formula (I) wherein
$R^5$ is
(a) alkyl, alkenyl, alkynyl, aryl or heterocyclo any of which may be optionally independently substituted as valence allows with one or more $Z^{1^d}$, $Z^{2^d}$ and $Z^{3^d}$; or
(b) —O$R^{6^a}$, —S$R^{9^a}$, SO$_2R^{9^a}$, SO$_2$N$R^{7^a}R^{8^a}$.

[4] In another embodiment, the present invention is directed to a compound of Formula (I) wherein
$Z^{1^b}$, $Z^{2^b}$ and $Z^{3^b}$ are optional substituents independently selected from alkyl, —$U^1$—OH, —$U^1$—O$Y^5$, —$U^1$—N$Y^2Y^3$, —$U^1$—C(O)$_t$H, —$U^1$—C(O)$_tY^5$, —$U^1$—C(O)—N$Y^2$—O$Y^5$, or —$U^1$—N($Y^4$)—C(O)—N$Y^2Y^3$, —$U^1$—N($Y^4$)—C(O)—$Y^1$, —$U^1$—N($Y^4$)—C(O)O—$Y^5$, —$U^1$—C(O)—N$Y^2Y^3$, —$U^1$—OC(O)—N$Y^2Y^3$;

$Z^{1^c}$ is
(a) —OH, —O$Y^5$ or
(b) aryl-$V^3$, wherein $V^3$ is H, —OH or —O$Y^5$;

$Z^{1^d}$, $Z^{2^d}$ and $Z^{3^d}$ are optional substituents independently selected from; (a) cyano, halo, —$U^1$—OH, —$U^1$—O$Y^5$, —$U^1$—N$Y^2Y^3$, —$U^1$—C(O)$_t$H, —$U^1$—C(O)$_tY^5$, —$U^1$—S(O)$_tY^1$, —$U^1$—C(O)—N$Y^2$—O$Y^5$, or —$U^1$—N($Y^4$)—C(O)—N$Y^2Y^3$, —$U^1$—N($Y^4$)—C(O)—$Y^1$, —$U^1$—N($Y^4$)—C(O)O—$Y^5$, —$U^1$—C(O)—N$Y^2Y^3$, —$U^1$—N($Y^4$)—S(O)$_2$—$Y^1$, —$U^1$—OC(O)—N$Y^2Y^3$.

(b) alkyl optionally substituted with one or more cyano, halo, —$U^1$—OH, —$U^1$—O$Y^5$, —$U^1$—N$Y^2Y^3$, —$U^1$—C(O)$_t$H, —$U^1$—C(O)$_tY^5$, —$U^1$—S(O)$_tY^1$, —$U^1$—N($Y^4$)—C(O)—$Y^1$, —$U^1$—N($Y^4$)—C(O)O—$Y^5$, —$U^1$—C(O)—N$Y^2Y^3$, —$U^1$—OC(O)—N$Y^2Y^3$.

[5] In another embodiment, the present invention is directed to a compound of Formula (I) wherein
$R^3$ is hydrogen;
$R^4$ is alkyl, haloalkyl, (hydroxy)alkyl, cycloalkyl, (cycloalkyl)alkyl, (heterocyclo)alkyl, (aryl)alkyl or (heteroaryl)alkyl and of which may be optionally independently substituted as valence allows with one or more $Z^{1^b}$, $Z^{2^b}$ and $Z^{3^b}$;

$R^5$ is
(a) alkynyl optionally substituted with $Z^{1^d}$ where $Z^{1^d}$ is aryl which may be further optionally independently substituted with one or more cyano, halo, —U$^1$—OH, —U$^1$—OY$^5$, —U$^1$—NY$^2$Y$^3$, —U$^1$—C(O)$_t$H, —U$^1$—C(O)$_t$Y$^5$, —U$^1$—S(O)$_t$Y, —U$^1$—N(Y$^4$)—U$^3$—NY$^2$Y$^3$, —U$^1$—N(Y$^4$)—U$^3$—Y$^5$, or —N(Y$^4$)—U$^3$—H;

(b) aryl optionally independently substituted as valence allows with one or more Z$^{1^d}$, Z$^{2^d}$ and Z$^{3^d}$; or (c) —OR$^{6^a}$, SR$^{9^a}$, SO$_2$R$^{9^a}$, SO$_2$NR$^{7^a}$R$^{8^a}$;

Z$^{1^b}$, Z$^{2^b}$ and Z$^{3^b}$ are optional substituents independently selected from —U$^1$—OH, —U$^1$—OY$^5$, —U$^1$—NY$^2$Y$^3$, —C(O)$_t$H, —C(O)$_t$Y$^5$, —U$^1$—C(O)—NY$^2$—OY$^5$, —N(Y$^4$)—C(O)—Y$^1$, N(Y$^4$)—C(O)O—Y$^5$, —C(O)—NY$^2$Y$^3$, —OC(O)—NY$^2$Y$^3$;

Z$^{1^c}$ is
(a) —OY$^5$ where Y$^5$ is aryl, or
(b) aryl-V$^3$, wherein V$^3$ is —OH or —OY$^5$ where Y$^5$ is alkyl;

Z$^{1^d}$, Z$^{2^d}$ and Z$^{3^d}$ are optional substituents independently selected from
(a) cyano, halo, —U$^1$—OH, —U$^1$—OY$^5$, —U$^1$—C(O)$_t$H, —U$^1$—C(O)$_t$Y$^5$, —S(O)$_t$Y$^1$, or
(b) alkyl optionally substituted with one or more cyano, halo, —OH, —OY$^5$, NY$^2$Y$^3$, —C(O)—NY$^2$Y$^3$, —C(O)—NY$^2$—OY$^5$, —N(Y$^4$)—C(O)—Y$^1$, —N(Y$^4$)—C(O)O—Y$^5$, —N(Y$^4$)—S(O)$_2$—Y$^1$, —C(O)$_t$H, —C(O)$_t$Y$^5$, —S(O)$_t$Y$^1$, —N(Y$^4$)—U$^2$—Y, or —N(Y$^4$)—U$^2$—H., where U$^1$ is a bond, alkylenyl or —O—U$^3$—.

[6] In another embodiment, the present invention is directed to a compound of Formula (I) wherein
R$^1$ is alkyl; and
R$^2$ is hydrogen.

[7] In another embodiment, the present invention is directed to a compound of Formula (I) wherein
R$^5$ is
(a) phenyl, pyridyl, pyrimidinyl, or acetyleneyl, any of which may be optionally independently substituted as valence allows with one or more Z$^{1^d}$, Z$^{2^d}$ and Z$^{3^d}$; or
(b) —OR$^{6^a}$, —SR$^{9^a}$, SO$_2$R$^{9^a}$, SO$_2$NR$^{7^a}$R$^{8^a}$;
R$^{6^a}$ is alkyl substituted with which may be optionally independently substituted as valence allows with Z$^{1^c}$, Z$^{2^c}$ and Z$^{3^c}$;
Z$^{1^c}$ is
(a) —OH, —OY$^5$ or
(b) aryl-V$^3$, wherein V$^3$ is H, —OH or —OY$^5$; Y$^5$ is alkyl.

[8] In another embodiment, the present invention is directed to a compound of Formula (I) wherein
Z$^{1^d}$, Z$^{2^d}$ and Z$^{3^d}$ are optional substituents independently selected from;
cyano, halo, —U$^1$—OH, —U$^1$—Y$^5$, —U$^1$—NY$^2$Y$^3$, —U$^1$—C(O)$_t$H, —U$^1$—C(O)$_t$Y$^5$, —U$^1$—S(O)$_t$Y$^1$, —U$^1$—C(O)—NY$^2$—OY$^5$, or —U$^1$—N(Y$^4$)—C(O)—NY$^2$Y$^3$, —U$^1$—N(Y$^4$)—C(O)—Y$^1$, —U$^1$—N(Y$^4$)—C(O)O—Y$^5$, —U$^1$—C(O)—NY$^2$Y$^3$, —U$^1$—N(Y$^4$)—S(O)$_2$—Y$^1$, —U$^1$—OC(O)—NY$^2$Y$^3$;
wherein
U$^1$ is a bond, alkylenyl or —O—U$^3$— and Y$^1$, Y$^2$, Y$^3$, Y$^4$, and Y$^5$ are independently selected from H or alkyl or haloalkyl.

[9] In another embodiment, the present invention is directed to a compound of Formula (I) wherein, wherein the compound is selected from the examples.

In another embodiment, the present invention is directed to a pharmaceutical composition comprising (a) at least one compound of Formula (I), or a pharmaceutically acceptable salt, hydrate or prodrug thereof, and (b) a pharmaceutically-acceptable carrier or diluent.

In another embodiment, the present invention is directed to a method of treating an inflammatory or immune disease or disorder comprising administering to a mammal in need thereof a therapeutically-effective amount of at least one compound of Formula (I).

In another embodiment, the present invention is directed to a method of treating an inflammatory or immune disease or disorder in which the inflammatory or immune disease is selected from rheumatoid arthritis, asthma, inflammatory bowel disease, chronic obstructive pulmonary disease, and psoriasis.

In another embodiment, the present invention is directed to a method of treating an inflammatory or immune disease or disorder in which the inflammatory or immune disease is selected from rheumatoid arthritis.

In another embodiment, the present invention is directed to a method of treating an inflammatory or immune disease or disorder in which the inflammatory or immune disease is selected from asthma.

In another embodiment, the present invention is directed to a method of treating an inflammatory or immune disease or disorder in which the inflammatory or immune disease is selected from inflammatory bowel disease.

In another embodiment, the present invention is directed to a method of treating an inflammatory or immune disease or disorder in which the inflammatory or immune disease is selected from chronic obstructive pulmonary disease.

In another embodiment, the present invention is directed to a method of treating an inflammatory or immune disease or disorder in which the inflammatory or immune disease is selected from psoriasis.

In another embodiment, the present invention is directed to compounds of Formula (I) for use in therapy.

In another embodiment, the present invention is directed to the use of compounds of Formula (I) in the preparation of a medicament for treating inflammatory or immune disease.

In another embodiment, the present invention is directed to compounds of Formula (I) wherein R$^1$ is hydrogen or alkyl.

In another embodiment, the present invention is directed to compounds of Formula (I) wherein R$^1$ is alkyl.

In another embodiment, the present invention is directed to compounds of Formula (I) wherein R$^2$ is hydrogen or alkyl.

In another embodiment, the present invention is directed to compounds of Formula (I) wherein R$^2$ is hydrogen.

In another embodiment, the present invention is directed to compounds of Formula (I) wherein R$^3$ and R$^4$ are independently
(a) hydrogen,
(b) alkyl, haloalkyl, (hydroxy)alkyl, cycloalkyl, (cycloalkyl)alkyl, (heterocyclo)alkyl, (aryl)alkyl or (heteroaryl)alkyl and of which may be optionally independently substituted as valence allows with one or more Z$^{1^b}$, Z$^{2^b}$ and Z$^{3^b}$; or
(c) R$^3$ and R$^4$ together with the nitrogen atom to which they are attached combine to form a heterocyclo ring optionally independently substituted as valence allows with one or more Z$^{1^b}$, Z$^{2^b}$ and Z$^{3^b}$.

In another embodiment, the present invention is directed to compounds of Formula (I) wherein
R$^3$ is hydrogen;
R$^4$ is alkyl, haloalkyl, (hydroxy)alkyl, cycloalkyl, (cycloalkyl)alkyl, (heterocyclo)alkyl, (aryl)alkyl or (heteroaryl)alkyl and of which may be optionally independently substituted as valence allows with one or more $Z^{1^b}$, $Z^{2^b}$ and $Z^{3^b}$.

In another embodiment, the present invention is directed to compounds of Formula (I) wherein $R^5$ is
(a) alkyl, alkenyl, alkynyl, aryl or heterocyclo any of which may be optionally independently substituted as valence allows with one or more $Z^{1^d}$, $Z^{2^d}$ and $Z^{3^d}$; or
(b) —$OR^{6^a}$, —$SR^{9^a}$, $SO_2R^{9^a}$, $SO_2NR^{7^a}R^{8^a}$.

In another embodiment, the present invention is directed to compounds of Formula (I) wherein $R^5$ is
(a) alkynyl optionally substituted with $Z^1{}_d$ where $Z^{1^d}$ is aryl which may be further optionally independently substituted with one or more cyano, halo, —$U^1$—OH, —$U^1$—$OY^5$, —$U^1$—$NY^2Y^3$, —$U^1$—$C(O)_tH$, —$U^1$—$C(O)_tY^5$, —$U^1$—$S(O)_tY^1$, —$U^1$—$N(Y^4)$—$U^3$—$NY^2Y^3$, —$U^1$—$N(Y^4)$—$U^3$—$Y^5$, or —$N(Y^4)$—$U^3$—H;
(b) aryl optionally independently substituted as valence allows with one or more $Z^1{}_d$, $Z^{2^d}$ and $Z^{3^d}$; or
(c) $OR^{6^a}$, $SR^{9^a}$, $SO_2R^{9^a}$, $SO_2NR^{7^a}R^{8^a}$.

In another embodiment, the present invention is directed to compounds of Formula (I) wherein $R^5$ is
(a) phenyl, pyridyl, pyrimidinyl, or acetyleneyl, any of which may be optionally independently substituted as valence allows with one or more $Z^{1^d}$, $Z^{2^d}$ and $Z^{3^d}$; or
(b) —$OR^{6^a}$, —$SR^{9^a}$, $SO_2R^{9^a}$, $SO_2NR^{7^a}R^{8^a}$.

In another embodiment, the present invention is directed to compounds of Formula (I) wherein $Z^{1^c}$ is
(a) —OH, —$OY^5$ or
(b) aryl-$V^3$, wherein $V^3$ is H, —OH or —$OY^5$;
$Z^{1^d}$, $Z^{2^d}$ and $Z^{3^d}$ are optional substituents independently selected from; (a) cyano, halo, —$U^1$—OH, —$U^1$—$OY^5$, —$U^1$—$NY^2Y^3$, —$U^1$—$C(O)_tH$, —$U^1$—$C(O)_tY^5$, —$U^1$—$S(O)_tY^1$, —$U^1$—$C(O)$—$NY^2$—$OY^5$, or —$U^1$—$N(Y^4)$—$C(O)$—$NY^2Y^3$, —$U^1$—$N(Y^4)$—$C(O)$—$Y^1$, —$U^1$—$N(Y^4)$—$C(O)O$—$Y^5$, —$U^1$—$C(O)$—$NY^2Y^3$, —$U^1$—$N(Y^4)$—$S(O)_2$—$Y^1$, —$U^1$—$OC(O)$—$NY^2Y^3$.
(b) alkyl optionally substituted with one or more cyano, halo, —$U^1$—OH, —$U^1$—$OY^5$, —$U^1$—$NY^2Y^3$, —$U^1$—$C(O)_tH$, —$U^1$—$C(O)_tY^5$, —$U^1$—$S(O)_tY^1$, —$U^1$—$N(Y^4)$—$C(O)$—$Y^1$, —$U^1$—$N(Y^4)$—$C(O)O$—$Y^5$, —$U^1$—$C(O)$—$NY^2Y^3$, —$U^1$—$OC(O)$—$NY^2Y^3$.

In another embodiment, the present invention is directed to compounds of Formula (I) wherein $Z^{1^c}$ is
(a) —$OY^5$ where $Y^5$ is aryl, or
(b) aryl-$V^3$, wherein $V^3$ is —OH or —$OY^5$ where $Y^5$ is alkyl;

In another embodiment, the present invention is directed to compounds of Formula (I) wherein $Z^{1^c}$ is
(a) —OH, —$OY^5$ or
(b) aryl-$V^3$, wherein $V^3$ is H, —OH or —$OY^5$.

In another embodiment, the present invention is directed to compounds of Formula (I) wherein $Z^{1^b}$, $Z^{2^b}$ and $Z^{3^b}$ are optional substituents independently selected from alkyl, —$U^1$—OH, —$U^1$—$OY^5$, —$U^1$—$NY^2Y^3$, —$U^1$—$C(O)_tH$, —$U^1$—$C(O)_tY^5$, —$U^1$—$C(O)$—$NY^2$—$OY^5$, or —$U$—$N(Y^4)$—$C(O)$—$NY^2Y^3$, —$U^1$—$N(Y^4)$—$C(O)$—$Y^1$, —$U^1$—$N(Y^4)$—$C(O)O$—$Y^5$, —$U^1$—$C(O)$—$NY^2Y^3$, —$U^1$—$OC(O)$—$NY^2Y^3$.

In another embodiment, the present invention is directed to compounds of Formula (I) wherein $Z^{1^b}$, $Z^{2^b}$ and $Z^{3^b}$ are optional substituents independently selected from —$U^1$—OH, —$U^1$—$OY^5$, —$U^1$—$NY^2Y^3$, —$C(O)_tH$, —$C(O)_tY^5$, —$U^1$—$C(O)$—$NY^2$—$OY^5$, —$N(Y^4)$—$C(O)$—$Y^1$, $N(Y^4)$—$C(O)O$—$Y^5$, —$C(O)$—$NY^2Y^3$, —$OC(O)$—$NY^2Y^3$.

In another embodiment, the present invention is directed to compounds of Formula (I) wherein $Z^{1^d}$, $Z^{2^d}$ and $Z^{3^d}$ are optional substituents independently selected from
(a) cyano, halo, —$U^1$—OH, —$U^1$—$OY^5$, —$U^1$—$C(O)_tH$, —$U^1$—$C(O)_tY^5$, —$S(O)_tY^1$, or
(b) alkyl optionally substituted with one or more cyano, halo, —OH, —$OY^5$, $NY^2Y^3$, —$C(O)$—$NY^2Y^3$, —$C(O)$—$NY^2$—$OY^5$, —$N(Y^4)$—$C(O)$—$Y^1$, —$N(Y^4)$—$C(O)O$—$Y^5$, —$N(Y^4)$—$S(O)_2$—$Y^1$, —$C(O)_tH$, —$C(O)_tY^5$, —$S(O)_tY^1$, —$N(Y^4)$—$U^2$—Y, or —$N(Y^4)$—$U^2$—H, where $U^1$ is a bond, alkylenyl or —O—$U^3$—.

In another embodiment, the present invention is directed to compounds of Formula (I) wherein $Z^{1^d}$, $Z^{2^d}$ and $Z^{3^d}$ are optional substituents independently selected from
cyano, halo, —$U^1$—OH, —$U^1$—$OY^5$, —$U^1$—$NY^2Y^3$, —$U^1$—$C(O)_tH$, —$U^1$—$C(O)_tY^5$, —$U^1$—$S(O)_tY^1$, —$U^1$—$C(O)$—$NY^2$—$OY^5$, or —$U^1$—$N(Y^4)$—$C(O)$—$NY^2Y^3$, —$U^1$—$N(Y^4)$—$C(O)$—$Y^1$, —$U^1$—$N(Y^4)$—$C(O)O$—$Y^5$, —$U^1$—$C(O)$—$NY^2Y^3$, —$U^1$—$N(Y^4)$—$S(O)_2$—$Y^1$, —$U^1$—$OC(O)$—$NY^2Y$ The invention may be embodied in other specific forms without departing from the spirit or essential attributes thereof. This invention also encompasses all combinations of alternative aspects of the invention noted herein. It is understood that any and all embodiments of the present invention may be taken in conjunction with any other embodiment to describe additional embodiments of the present invention. Furthermore, any elements of an embodiment are meant to be combined with any and all other elements from any of the embodiments to describe additional embodiments.

DEFINITIONS

The following are definitions of terms used in this specification. The initial definition provided for a group or term herein applies to that group or term throughout the present specification, individually or as part of another group, unless otherwise indicated.

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The term "substituted," as used herein, means that any one or more hydrogens on the designated atom or ring is replaced with a selection from the indicated group, provided that the designated atom's or ring atom's normal valency is not exceeded, and that the substitution results in a stable compound. When a substitent is keto (i.e., =O), then 2 hydrogens on the atom are replaced.

When any variable (e.g., $R^a$) occurs more than one time in any constituent or formula for a compound, its definition at each occurrence is independent of its definition at every other occurrence. Thus, for example, if a group is shown to be substituted with 0–2 $R^a$, then said group may optionally be substituted with up to two $R^a$ groups and $R^a$ at each occurrence is selected independently from the definition of $R^a$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

The term "alkyl" as used herein by itself or as part of another group refers to straight and branched chain hydrocarbons, containing 1 to 20 carbons, preferably 1 to 10 carbons, more preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like. Lower alkyl groups, that is, alkyl groups of 1 to 4 carbon atoms, are often most preferred.

The term "alkenyl" as used herein by itself or as part of another group refers to straight or branched chain radicals of 2 to 20 carbons, preferably 2 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like.

The term "alkynyl" as used herein by itself or as part of another group refers to straight or branched chain hydrocarbon groups having 2 to 12 carbon atoms, preferably 2 to 4 carbon atoms, and at least one triple carbon to carbon bond, such as ethynyl, 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like.

When the term "alkyl" is used together with another group, such as in "(aryl)alkyl", this conjunction is meant to refer to a substituted alkyl group wherein at least one of the substituents is the specifically named group in the conjunction. For example, "(aryl)alkyl" refers to a substituted alkyl group as defined above wherein at least one of the substituents is an aryl, such as benzyl.

Where alkyl groups as defined above have single bonds for attachment to two other groups, they are termed "alkylene" groups. Similarly, where alkenyl groups as defined above and alkynyl groups as defined above, respectively, have single bonds for attachment to two other groups, they are termed "alkenylene groups" and "alkynylene groups" respectively. Examples of alkylene, alkenylene and alkynylene groups include:

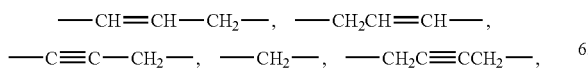

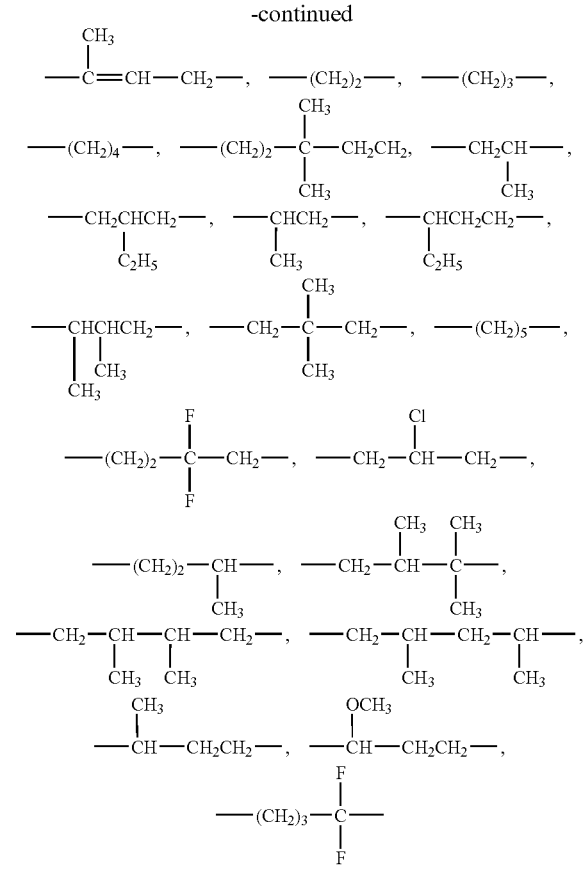

and the like. Alkylene groups may be optionally independently to substituted as valence allows with one or more groups provided in the definition of $Z^1$.

The term "cycloalkyl" as used herein by itself or as part of another group refers to saturated and partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 7 carbons, forming the ring. The rings of multi-ring cycloalkyls may be either fused, bridged and/or joined through one or more spiro union to 1 or 2 aromatic, cycloalkyl or heterocyclo rings. Exemplary cycloalkyl groups include cyclopropyl, cyclobutyl, cyclopentyl, cyclohexyl, cycloheptyl, cyclooctyl, cyclodecyl, cyclododecyl, cyclopentenyl, cyclohexenyl, cycloheptenyl, cyclooctenyl, cyclohexadienyl, cycloheptadienyl,

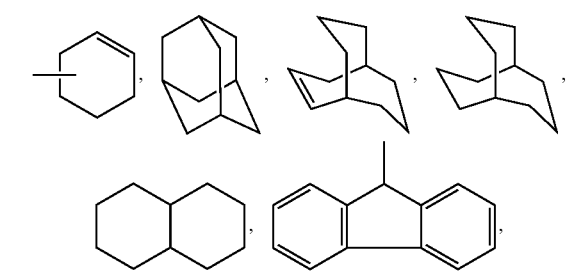

-continued

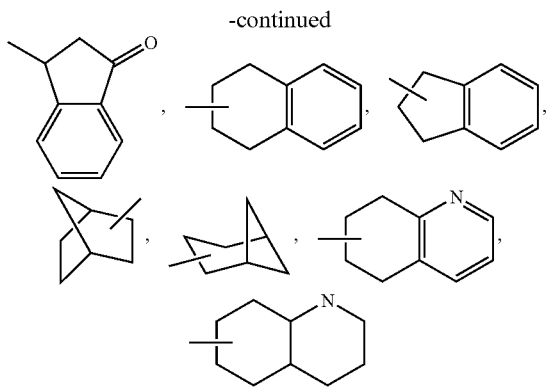

and the like.

The term "cycloalkylene" as employed herein refers to a "cycloalkyl" group which includes free bonds and thus is a linking group such as

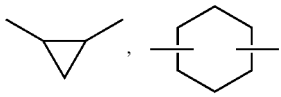

and the like.

One skilled in the field will understand that, when the designation "CO$_2$" is used herein, this is intended to refer to the group

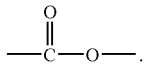

The term "alkoxy" refers to an alkyl or substituted alkyl group as defined above bonded through an oxygen atom (—O—), i.e., the groups —OR$_d$, wherein R$_d$ is alkyl or substituted alkyl.

The term "alkylthio" refers to an alkyl or substituted alkyl group as defined above bonded through a sulfur atom (—S—), i.e., the groups —SR$_d$, wherein R$_d$ is alkyl or substituted alkyl.

The term "acyl" refers to a carbonyl group linked to an organic radical, more particularly, the group C(=O)R$_g$, wherein R$_g$ can be selected from alkyl, alkenyl, substituted alkyl, or substituted alkenyl, as defined herein.

The term "alkoxycarbonyl" refers to a carboxy group

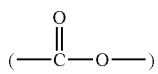

linked to an organic radical (CO$_2$R$_g$), wherein R$_g$ is as defined above for acyl.

The term "halo" or "halogen" refers to chloro, bromo, fluoro and iodo.

The term "haloalkyl" means a substituted alkyl having one or more halo substituents. For example, "haloalkyl" includes mono, bi, and trifluoromethyl.

The term "haloalkoxy" means an alkoxy group having one or more halo substituents. For example, "haloalkoxy" includes OCF$_3$.

The terms "ar" or "aryl" as used herein by itself or as part of another group refer to aromatic homocyclic (i.e., hydrocarbon) monocyclic, bicyclic or tricyclic aromatic groups containing 6 to 14 carbons in the ring portion (such as phenyl, biphenyl, naphthyl (including 1-naphthyl and 2-naphthyl) and antracenyl) and may optionally include one to three additional rings (either cycloalkyl, heterocyclo or heteroaryl) fused thereto. Examples include:

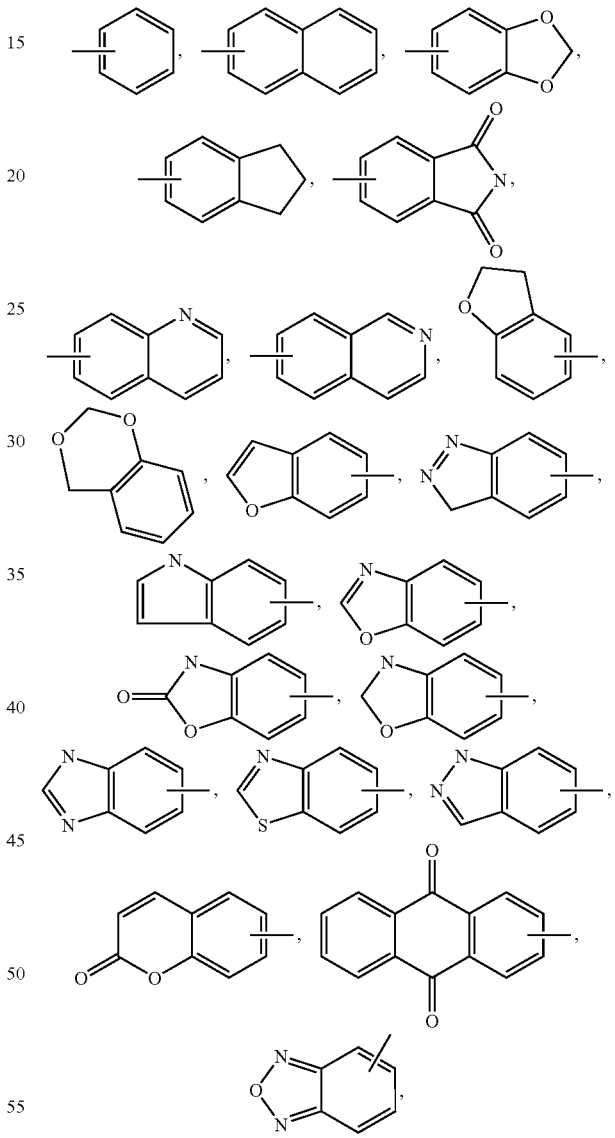

and the like.

The term "heteroaryl" as used herein by itself or as part of another group refers to monocyclic and bicyclic aromatic rings containing from 5 to 10 atoms, which includes 1 to 4 hetero atoms such as nitrogen, oxygen or sulfur, and such rings fused to an aryl, cycloalkyl, heteroaryl or heterocyclo ring, where the nitrogen and sulfur heteroatoms may optionally be oxidized and the nitrogen heteroatoms may optionally be quaternized. Examples of heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl, indolyl, benzothienyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl, carbazolyl, benzidolyl, phenanthrollinyl, acridinyl, phenanthridinyl, xanthenyl

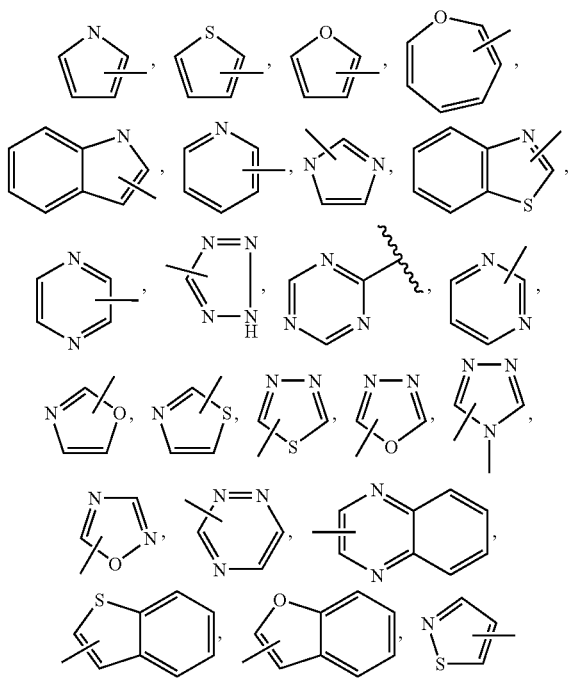

and the like.

In compounds of formula (I), preferred heteroaryl groups include

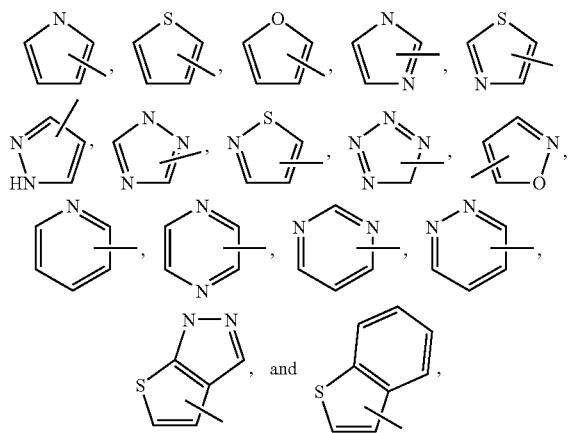

and the like, which optionally may be substituted at any available carbon or nitrogen atom.

The terms "heterocyclic" or "heterocyclo" as used herein by itself or as part of another group refer to optionally substituted, fully saturated or partially unsaturated cyclic groups (for example, 3 to 13 member monocyclic, 7 to 17 member bicyclic, or 10 to 20 member tricyclic ring systems, preferably containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system, where valance allows. The rings of multi-ring heterocycles may be either fused, bridged and/or joined through one or more spiro unions. Exemplary heterocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl,

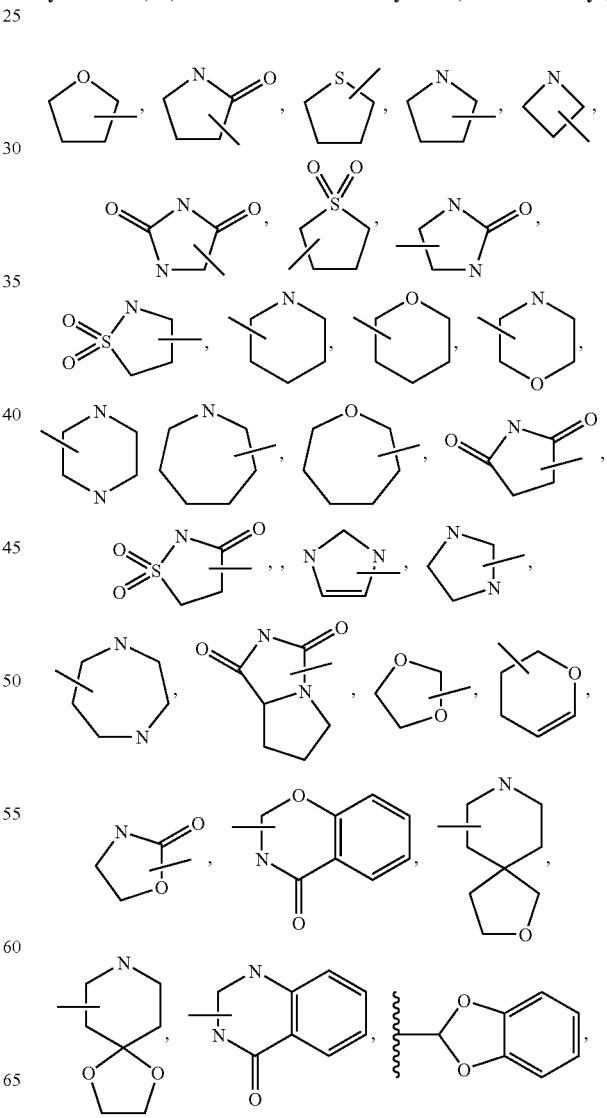

-continued

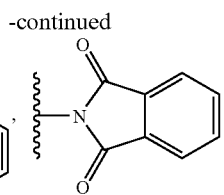

and the like.

Preferred heterocyclo groups in compounds of formula (I) include

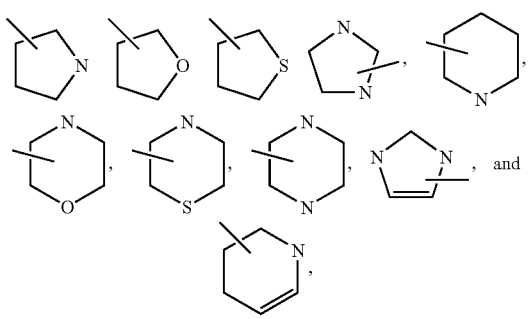

which optionally may be substituted.

The term "ring" encompasses homocyclic (i.e., as used herein, all the ring atoms are carbon) or "heterocyclic" (i.e., as used herein, the ring atoms include carbon and one to four heteroatoms selected from N, O and/or S, also referred to as heterocyclo), where, as used herein, each of which (homocyclic or heterocyclic) may be saturated or partially or completely unsaturated (such as heteroaryl).

Unless otherwise indicated, when reference is made to a specifically-named aryl (e.g., phenyl), cycloalkyl (e.g., cyclohexyl), heterocyclo (e.g., pyrrolidinyl) or heteroaryl (e.g., imidazolyl), unless otherwise specifically indicated the reference is intended to include rings having 0 to 3, preferably 0 to 2, substituents selected from those recited above for the aryl, cycloalkyl, heterocyclo and/or heteroaryl groups, as appropriate.

The term "heteroatoms" shall include oxygen, sulfur and nitrogen.

The term "carbocyclic" means a saturated or unsaturated monocyclic or bicyclic ring in which all atoms of all rings are carbon. Thus, the term includes cycloalkyl and aryl rings. The carbocyclic ring may be substituted in which case the substituents are selected from those recited above for cycloalkyl and aryl groups.

When the term "unsaturated" is used herein to refer to a ring or group, the ring or group may be fully unsaturated or partially unsaturated.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds. One skilled in the field may make the appropriate selections for B and X to provide stable compounds.

The term "optionally independently substituted as valence allows with one or more" substituent means that any of the valences may be independently substituted with up to that number of substituents. While not limiting the invention, in specific instances, this means that substrate is substituted with 0–5 substituents, 0–4 substituents, 0–3 substituents, 0–2 substituents, 0–1 substituents or no substituents.

The compounds of formula I form salts which are also within the scope of this invention. Reference to a compound of the formula I herein is understood to include reference to salts thereof, unless otherwise indicated. The term "salt(s)", as employed herein, denotes acidic and/or basic salts formed with inorganic and/or organic acids and bases. In addition, when a compound of formula I contains both a basic moiety, such as, but not limited to an amine or a pyridine ring, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the formula I may be formed, for example, by reacting a compound of the formula I with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines [formed with N,N-bis(dehydroabietyl)ethylenediamine], N-methyl-D-glucamines, N-methyl-D-glucamides, t-butyl amines, and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Compounds of the formula I, and salts thereof, may exist in their tautomeric form, in which hydrogen atoms are transposed to other parts of the molecules and the chemical bonds between the atoms of the molecules are consequently rearranged. It should be understood that all tautomeric forms, insofar as they may exist, are included within the invention. Additionally, inventive compounds may have trans and cis isomers and may contain one or more chiral centers, therefore existing in enantiomeric and diastereomeric forms. The invention includes all such isomers, as well as mixtures of cis and trans isomers, mixtures of diastereomers and racemic mixtures of enantiomers (optical isomers). When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials. When enantiomeric or diastereomeric products are prepared, they can be separated by conventional methods, for example, by chromatographic or fractional crystallization. The inventive compounds may be in the free or hydrate form.

In addition, compounds of formula I may have prodrug forms. Any compound that will be converted in vivo to provide the bioactive agent (i.e., a compound of formula I) is a prodrug within the scope and spirit of the invention.

For example, pro-drug compounds of formula I may be carboxylate ester moieties. A carboxylate ester may be conveniently formed by esterifying any of the carboxylic acid functionalities found on the disclosed ring structure(s). Various forms of prodrugs are well known in the art. For examples of such prodrug derivatives, see:

a) *Design of Prodrugs*, edited by H. Bundgaard, (Elsevier, 1985), and *Methods in Enzymology*, Vol. 42, at pp. 309–396, edited by K. Widder, et. al. (Academic Press, 1985);

b) *A Textbook of Drug Design and Development*, edited by Krosgaard-Larsen and H. Bundgaard, Chapter 5, "Design and Application of Prodrugs," by H. Bundgaard, atpp. 113–191 (1991);

c) H. Bundgaard, *Advanced Drug Delivery Reviews*, Vol. 8, p. 1–38 (1992);

d) H. Bundgaard, et al., *Journal of Pharmaceutical Sciences*, Vol. 77, p. 285 (1988); and e) N. Kakeya, et. al., *Chem Phar Bull*, Vol. 32, p. 692 (1984).

It should further be understood that solvates (e.g., hydrates) of the compounds of formula I are also with the scope of the present invention. Methods of solvation are generally known in the art.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or in combination with other active ingredients effective to inhibit MCP-1 or effective to treat or prevent inflammatory disorders.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

METHODS OF PREPARATION

The inventive compounds may be prepared by methods such as those illustrated in the following Schemes A1 to C2. Starting materials are commercially available or can be readily prepared by one of ordinary skill in the art, and/or modifications can be made to the methods of Schemes A1 to C2 by one skilled in the art, using known methods. For all of the schemes and compounds, the groups $R^1$, $R^2$, $R^3$, $R^4$, and $R^5$ are as described herein for a compound of formula I, unless otherwise indicated, and appropriate starting materials may be selected by one skilled in the field having the desired groups. Solvents, temperatures, pressures, and other reaction conditions may readily be selected as appropriate by one of ordinary skill in the art. For example, in these schemes chlorinating agents may include phosphorous oxychloride, catalytic agents may include metals such as Pd, and solvents may be selected from 1,2-dichlorobenzene, methylene chloride, DMF, alcohols, ethers, THF, dioxane, acetonitrile, water, mixtures of ethers and water, and the like.

"Cross-coupling" or coupling reactions as used in the schemes and examples may include all cross-coupling methods known by those skilled in the art. Such methods include Stille-type coupling (reacting a vinyl or aromatic triflate, bromide, iodide or thiomethylether with a tin reagent), Suzuki-type coupling (reacting a zinc, magnesium or boronate derivative), Heck coupling, and Sonogashira coupling all of which are catalyzed either by palladium(0), palladium (II), nickel(0) or nickel(II)). Copper iodide, copper (I) thiophene carboxylate, copper bromide dimethylsulfide complex, lithium chloride, zinc chloride, triphenylarsine, tris(2-furyl)phosphine or tris(2,4,6-trimethoxyphenyl)phosphine advantageously may also be added. When a boronic acid derivative is used, the reaction may proceed in the presence of an inorganic base such as sodium carbonate or potassium phosphate or carbonate. The cross-coupling reactions are performed in an inert organic solvent.

Compounds of formula I are conveniently prepared by a convergent synthesis by the condensation of key intermediates A1.6 and B1.4 followed by further elaboration. Key intermediate A1.6 may be prepared from commercially available ethyl 2-mercaptoimidazole-4-carboxylate, A1.1, as shown in Scheme A1. The mercapto group is first methylated to give A1.2, followed by N-substituted either by classical alkylation or by reaction with vinyl, aryl or heteroaryl boronic acids, or vinyl, aryl or heteroaryl tin reagents in the presence of copper salts such as copper acetate in air with or without the presence of an oxidant such as pyridine N-oxide to give A1.3. A1.3 is transesterified to give A1.4, which is chlorinated to provide A1.5. Oxidation of A1.5 with reagents such as m-chloroperbenzoic acid or oxone provided key intermediate A1.6. to give VII.

Scheme A1

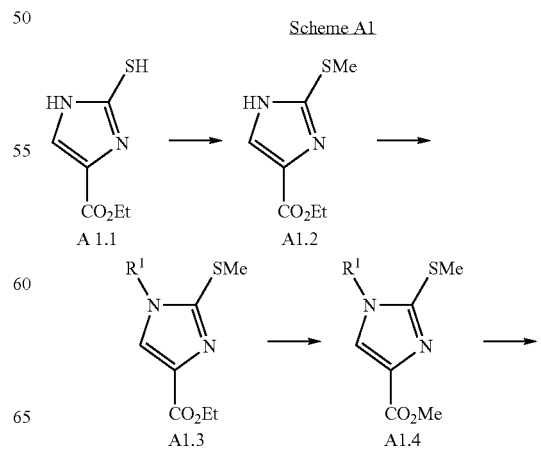

-continued

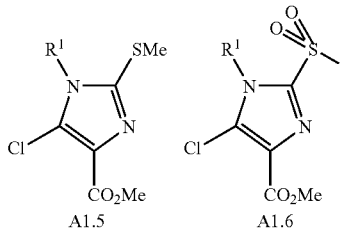

Alternatively, compound A1.4 may be prepared as depicted in Scheme A2. In this instance commercially available A2.1 is condensed with A2.2 to provide intermediate A2.3. Reaction of A2.3 with an appropriately substituted primary amine provides imidazoles of structure A1.4. These intermediates may be further elaborated as described in Scheme A1.

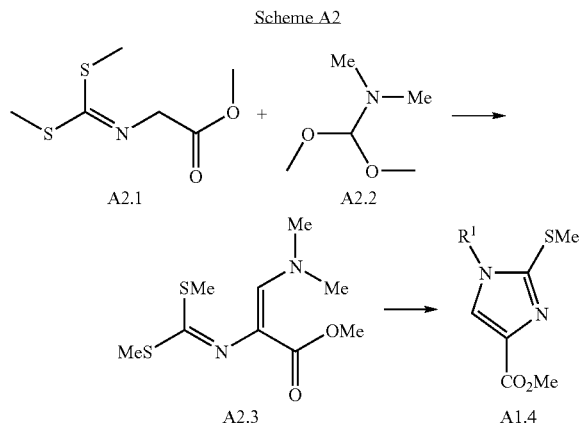

Key intermediate B1.4 may be conveniently prepared by several methods. Scheme B1 outlines a very general synthesis to these important intermediates. In this example either a carboxylic acid (B1.1, L=OH) is coupled with aminoguanidine (B1.2) to provide B1.3. Or the coupling can be carried out using any of the many methods for the formation of amide-like bonds known to one skilled in the art of organic synthesis. These methods include but are not limited to conversion of the acid to the corresponding acid chloride, or use of standard coupling procedures such as the azide method, mixed carbonic acid anhydride (isobutyl chloroformate) method, carbodiimide (dicyclohexylcarbodiimide, diisopropylcarbodiimide, or water-soluble carbodiimides) method, active ester (p-nitrophenyl ester, N-hydroxysuccinic imido ester) method, carbonyldiimidazole method, phosphorus reagents such as BOP-Cl. Some of these methods (especially the carbodiimide) can be enhanced by the addition of 1-hydroxybenzotriazole. In the case of coupling with aminoguanidine even unactivated esters such as alkyl esters can be readily coupled. Either conventional or microwave heating of B1.3 neat or in the presence of a solvent will provide aminotriazole B1.4. In some instances it is more convenient not to isolate B1.3 but to heat the reaction mixture to directly affect coupling and cyclization to B1.4 directly.

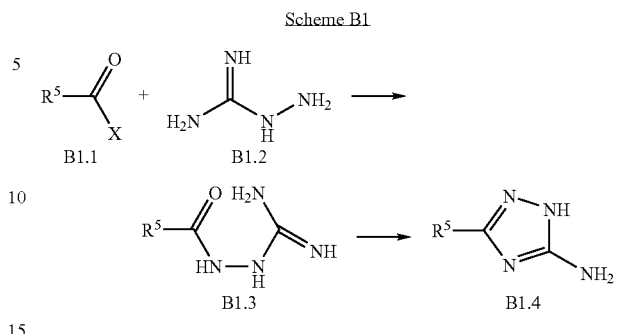

X = Cl, —OH, —OAlkyl, —Oaryl, —Oheterocyclic

A general synthesis of final compounds I, is shown in Scheme C1. Intermediate A1.5 or A1.6 is condensed with B1.4 to give triazolopurine intermediate C1.1. In the case where C1.1 possesses a thioalkyl ether a variety of groups may be introduced at this position by reaction with either boronic acids (for example see Liebeskind L. S. and Srogl, J. in *Org. Lett.* 2002, 4, pp 979–981) or aryl tin reagents (for example Alphonse, F-A., et. al. in *Org. Lett.* 2003, 5, pp 803–805) in the presence of palladium and copper (I) to provide C1.2 with diverse $R^2$ substituents. In the case where C1.1 possesses a methanesulfonyl group, this group may be displaced by amines, mercaptans or alkoxides to produce C1.2 or may be removed by reduction to provide hydrogen as the $R^2$ substituent in C1.2. Intermediate C1.2 is then reacted with a reagent such as phosphorus oxychloride, phosphorus oxybromide, or trifluoromethanesulfonic anhydride to produce intermediate C1.3. C1.3 is then converted to I by condensation with appropriate amines.

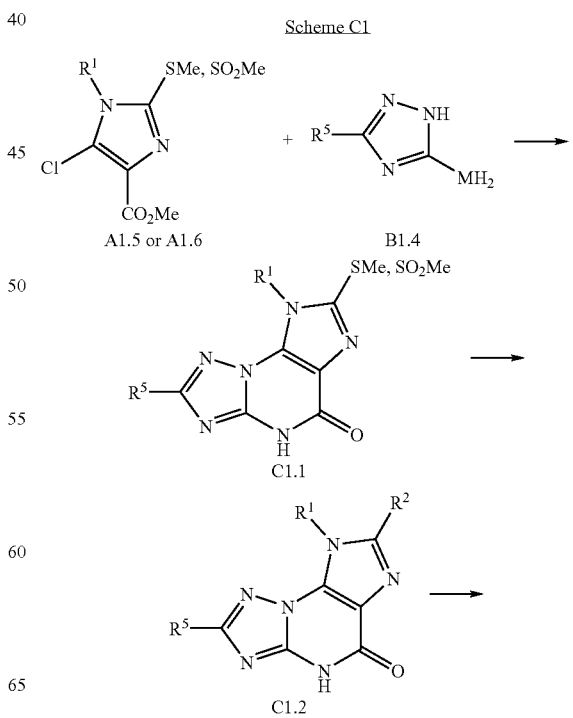

-continued

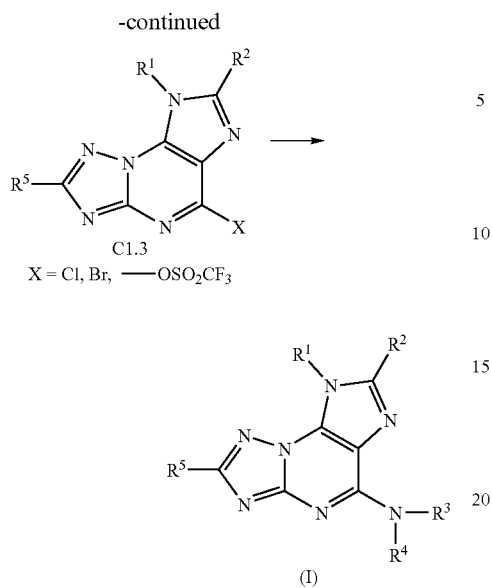

X = Cl, Br, —OSO$_2$CF$_3$

An alternative route to compounds of formula (I) which permit late stage diversification of R$^5$ is depicted in Scheme C2. This synthesis starts by condensing commercially available 3-amino-5-methylthio-1,3,4-triazole, C2.1, with imidazole A1.6. to produce intermediate C2.2. Reductive removal of the methanesulfone group by hydride reagents such as lithium triethylborohydride to produce intermediate C2.3. Reaction of C2.3 with phosphorous oxychloride or similar reagent produces chloropyridine intermediate C2.4. Displacement of the chlorine by reaction with amines produces C2.5 which is a compound of formula (I). The methythio-ether of C2.5 can be replaced to alternative R$^5$ groups by reaction with a wide variety of boronic acid, tin reagents or nickel reagents as described above to produce compounds of formula (I).

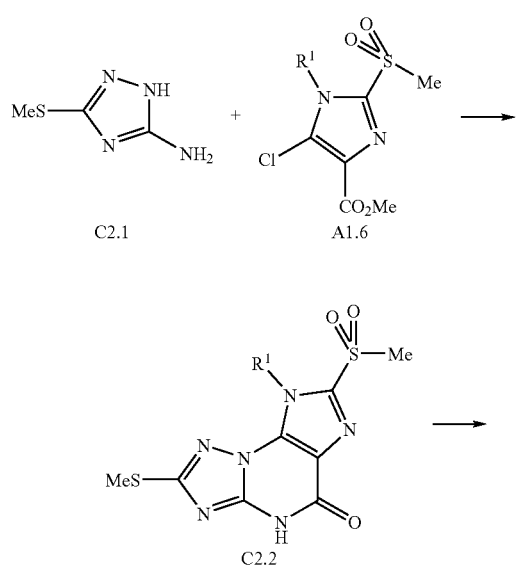

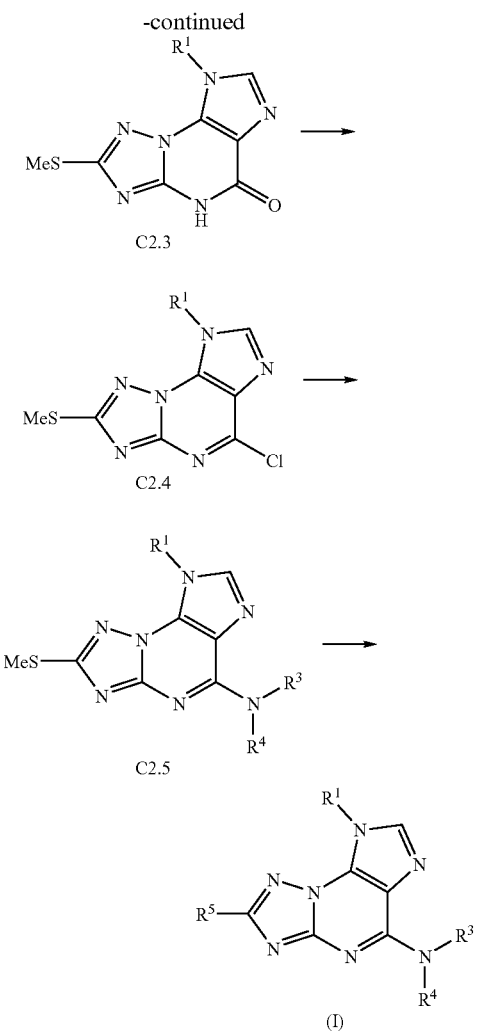

EXPERIMENTALS

Abbreviations

For ease of reference, the following abbreviations are employed herein, including in the methods of preparation hereinbefore and in the Examples that follow:
Ph=phenyl
Bz=benzyl
t-Bu=tertiary butyl
Me=methyl
Et=ethyl
Pr=propyl
Iso-P=isopropyl
MeOH=methanol
EtOH=ethanol
EtOAc=ethyl acetate
Boc=tert-butyloxycarbonyl
CBZ=carbobenzyloxy or carbobenzoxy or benzyloxycarbonyl
DMF=dimethyl formamide
DMSO=dimethyl sulfoxide
TEA=triethylamine
TFA=trifluoroacetic acid
THF=tetrahydrofuran KOH=potassium hydroxide
K₂CO₃=potassium carbonate
POCl₃=phosphorous oxychloride
KOtBu=potassium t-butoxide
HOBt=1-hydroxybenzotriazole hydrate
NaH=sodium hydride
NaOH=sodium hydroxide
Na₂S₂O₃=sodium thiosulfate
NCS=N-chlorosuccinimide
Pd=palladium
min.=minute(s)
L=liter
mL=milliliter
μL=microliter
g=gram(s)
mg=milligram(s)
mol=moles
mmol=millimole(s)
meq=milliequivalent
RT=room temperature
ret. t. =HPLC retention time (minutes)
sat or sat'd=saturated
aq.=aqueous
TLC=thin layer chromatography
HPLC=high performance liquid chromatography
LC/MS=high performance liquid chromatography/mass spectrometry
MS=mass spectrometry
NMR=nuclear magnetic resonance
mp=melting point The following Examples illustrate embodiments of the invention and are not intended to limit the scope of the claims. The products are designated according to the example and step number. For example the product of Example 1 Step A will be designated as 1A. These designations will represent the compound as a short name when it is used in subsequent reaction steps. In the following Examples, anhydrous reactions were performed under an atmosphere of nitrogen or argon using either commercially available dry solvents or freshly distilled solvents. Reactions which refer to heating by microwave irradiation were performed on a Smith Synthesizer™ capable of generating reaction temperatures between 60 and 250° C., and pressures of 0–290 pounds per square inch (PSI). Column chromatography was performed using EM Science silica gel 60 with the designated solvent system as eluant. HPLC purification was conducted using a Shimadzu LC8A with YMC S5 ODS or xTerra MS $C_{18}$ columns. HPLC purity determinations were done using either an HP 1090 DR5 with a diode array detector and a Waters Nova-Pak $C_{18}$ column, or a Shimadzu LC-10AS with a SPD-10AV UV-V detector and Waters xTerra $C_{18}$ column. Melting points were determined in an open capillary tube with a Thomas-Hoover melting point apparatus.

¹H-NMR spectra were recorded in DMSO (δ=2.50 ppm) using a 500 MHZ instrument (unless otherwise stated) and chemical shifts are expressed in parts per million (ppm or δ) with the solvent in use as an internal standard. Coupling constants are given in Hertz, and multiplets are designated as follows: singlet (s), doublet (d), triplet (t), quartet (q), multiplet (m), broad (br), and apparent (app).

Low resolution mass spectra were determined with a Finnigan Matt TSQ-7000 or SSQ-700, or with a Shimadzu LC-10AS coupled with Waters Micromass ZQ. HRMS were determined with a Finnigan Matt 900.

EXAMPLE 1

1-Methyl-4-methylamino-7-phenyl-triazolo[5,1-b]purine

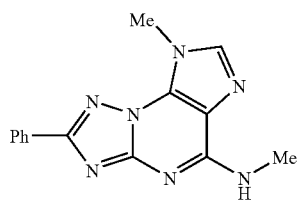

Example 1, Part A: Ethyl 2-methylthio-4-imidazole carboxylate

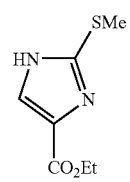

To a mixture of commercially available ethyl 2-mercapto-4-imidazole carboxylate (49.82 g, 289 mmol) and K₂CO₃ (79.92 g, 579 mmol) in DMF (1500 mL) was added MeI (18.55 mL, 298 mmol) at room temperature, with stirring. After 18 hrs, the reaction mixture was filtered. The filtrate was concentrated under high vacuum to remove DMF. The residue was then filtered through a silica gel pad with EtOAc, and concentrated. PhMe (200 mL) was then added, followed by addition of Hexanes (1000 mL), precipitating 1A (50.5 g, 94%) as a yellow solid. ¹H NMR (CDCl₃, 400 MHz): 7.69 (s, 1H), 4.35 (q, J=7.1 Hz, 2H), 2.67 (s, 3H), 1.35 (t, J=7.1 Hz, 3H).

Example 1, Part B: Methyl 1-methyl-2-methylthio-4-imidazolecarboxylate

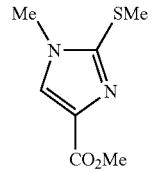

To a solution of 1A (50.5 g, 266 mmol) in THF (anhydrous, 1000 mL) was added NaH (60%, 14.3 g) at −78° C. After 1 h, MeI (18.5 mL, 297 mmol) was added. The mixture was then gradually warmed to 0° C. Upon completion of the reaction, filtration followed by concentration provided a residue, which was then dissolved in EtOAc/CHCl₃ (1500 mL, 2:1) and filtered to remove the solid. The filtrate was concentrated to give ethyl 1-methyl-2-methylthio-4-imidazolecarboxylate, which was dissolved in MeOH (1000 mL) and stirred in the presence of K₂CO₃ (10 g). After 3 days, it was filtered and the MeOH was removed under vacuum. The residue was passed through a silica gel pad with EtOAc, furnishing compound 1B (35.2 g, 67%) as a solid. $^1$H NMR (CDCl$_3$, 400 MHz): 7.48 (s, 1H), 3.74 (s, 3H), 3.50 (s, 3H), 2.54 (s, 3H); ESI m/z=187.05 [(M+H)$^+$; calcd for C$_7$H$_{11}$N$_2$O$_2$S: 187.05]

Alternatively, compound 1B can be prepared according to the following procedure:

Commercially available N-[Bis(methylthio)methylene] glycine methyl ester (5.06 g, 26.18 mmol) and N,N-Dimethylformamide dimethyl acetal (4.03 g, 31.41 mmol) were dissolved in N,N-dimethylformamide (10 mL) and heated to reflux under nitrogen for 4.5 h. The solvent was removed under reduced pressure and the product, 2-[[Bis(methylthio) methylene]amino]-3-(dimethylamino)-2-propenoic acid, methyl ester solidified (6.44 g, 99%) after storage at room temperature under high vacuum over night. $^1$H NMR (CDCl$_3$, 400 MHz): δ 6.96 (s, 1H); 3.68 (s, 3H); 2.95 (s, 6H); 2.53 (s, 3H); 2.49 (s, 3H). 2-[[Bis(methylthio)methylene]amino]-3-(dimethylamino)-2-propenoic acid, methyl ester (8.29 g, 33.39 mmol) and methylamine hydrochloride (2.71 g, 40.07 mmol) were added to methanol (150 mL) and heated at reflux for 32 h. The reaction mixture was cooled and concentrated with silica gel (~20 g). The mixture was placed on top of a silica gel column and the product eluted with 90% ethyl acetate 10% heptane. Concentration of the appropriate fractions provided 4.13 g (66%) of the title product as a yellow solid. LCMS (10% MeOH, 90% H$_2$O, 0.1% TFA to 90% MeOH, 10% H$_2$O, 0.1% TFA, 2 minute gradient with a Phenomenex S5 column 4.6×30 mm produced a retention time of 0.56 minutes, and a [M+H]$^+$ m/z=187.16.

Example 1, Part C: Methyl 1-methyl-2-methylthio-5-chloro-4-imidazolecarboxylate

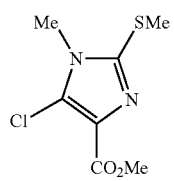

1C

A mixture of 1B (35.2 g, 189 mmol) and NCS (26.5 g, 198 mmol) was stirred in CH$_2$Cl$_2$ (1000 mL) at room temperature. After 18 hrs, concentration followed by extractive work-up with EtOAc/H$_2$O and filtration through a silica gel pad with EtOAc/Hex (50:50) provided compound 1C (39.8 g, 95%) as a solid. $^1$H NMR (CDCl$_3$, 400 MHz): 3.94 (s, 3H), 3.57 (s, 3H), 2.70 (s, 3H); ESI m/z=243.67 [(M+Na)$^+$; calcd for C$_7$H$_9$ClN$_2$O$_2$S+Na: 243.00]

Example 1, Part D: Methyl 1-methyl-2-methanesulfonyl-5-chloro-4-imidazolecarboxylate

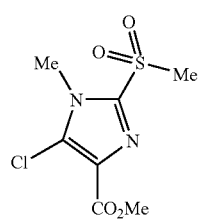

1D

A mixture of 1c (39.8 g, 180 mmol) and MCPBA (93.4 g) in CH$_2$Cl$_2$ (1000 mL) was stirred at room temperature for 6 h. NEt$_3$ (100 mL) was added to neutralize the acid, followed by addition of MgSO$_4$ to remove H$_2$O. It was then passed through a silica gel pad with EtOAc, furnishing compound 1D (38.1 g, 84%) as a white solid. $^1$H NMR (CDCl$_3$, 400 MHz): 3.89 (s, 3H), 3.87 (s, 3H), 3.40 (s, 3H); ESI m/z=253.06 [(M+H)$^+$; calcd for C$_7$H$_9$ClN$_2$O$_4$S+H: 253.00]

Example 1, Part E: 1-Methyl-2-methanesulfonyl-7-phenyl-4H-triazolo[5,1-b]purin-4-one

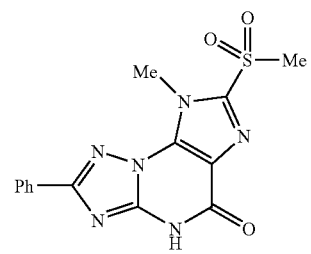

1E

A mixture of commercially available 5-amino-3-phenyltriazole (0.8938 g, 5.58 mmol), and 1D (1.0839 g, 4.29 mmol) was stirred vigorously at the presence of K$_2$CO$_3$ (5.591 g, 17.16 mmol) in DMF (anhydrous, 43 mL) at 100° C. in a sealed reaction vessel. After 18 h, the reaction mixture was filtered and the filtrate was concentrated under high vacuum to remove DMF. The residue was partitioned between ethyl acetate and water. The ethyl acetate extracts were combined and concentrated in vacuo. The residue was chromatographed via Reverse-Phase PREP HPLC [gradient 10% MeOH/90% water to 90% MeOH/10% water] providing 1E (360.2 mg, 25%) as a white solid $^1$H NMR (DMSO, 400 MHz): 12.3 (s, NH), 8.2 (d, 2H), 7.6 (m, 3H), 4.5 (s, 3H); 3.5(s, 3H) ESI m/z=344.35 [(M+H)$^+$; calcd for C$_{14}$H$_{12}$N$_6$O$_3$S+H: 345]; HPLC RT=2.777 min [4 min grad, 10% MeOH/90% water to 90% MeOH/10% water]

Example 1, Part F: 1-Methyl-7-phenyl-4H-triazolo[5,1-b]purin-4-one

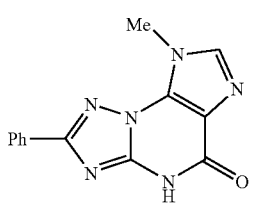

1F

A solution of 1E (48 mg, 0.139 mmol) in THF (anhydrous, 30 mL) was treated with LiBHEt$_3$ (1.0 M/THF, 1.6 mL) at −78° C. After 3 h the reaction mixture was allowed to slowly rise to 0° C. when it was carefully quenched with MeOH and concentrated in vacuo. The residue dissolved in ethyl acetate was treated with pH 7 buffer solution (40 mL), then neutralized with sat'd ammoniumchloride solution. The ethyl acetate extract was concentrated and chromatography using Reverse-Phase PREP HPLC provided compound 1F (30 mg, 81%) as a white solid. $^1$H NMR (d-MeOD, 400 MHz): 12.0 (s, NH), 8.0 (m, 3H), 7.4 (m, 3H), 4.7 (s, 3H); ESI m/z=266.26 [(M+H)$^+$; calcd for C$_{14}$H$_{11}$N$_5$O+H: 267]; HPLC RT=2.503 min [4 min grad, 10% MeOH/90% water to 90% MeOH/10% water]

Example 1, Part G: 4-Chloro-1-methyl-7-phenyl-1H-[1,2,4]triazolo[5,1-b]purine

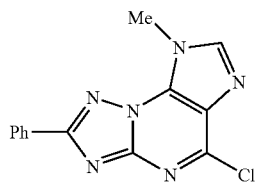

1G

A mixture of 1F (150.0 mg, 0.5639 mmoles) in 10 ml phosphorous oxychloride was heated at 100° C. for 16 h. The reaction mixture was cooled to room temperature and concentrated in vacuo. The crude residue was quenched with ice/water, and extracted with ethyl acetate. The ethyl acetate extracts were combined, washed with water, dried ($Na_2SO_4$), and concentrated to give 170 mg. product as a tan solid. $^1$H NMR (d-MeOD, 400 MHz): 8.2 (m, 3H), 7.4 (m, 3H), 4.3 (s, 3H); ESI m/z=284.70 [(M+H)$^+$; calcd for $C_{14}H_{11}N_5O+H$: 285]; HPLC RT=2.803 min [4 min grad, 10% MeOH/90% water to 90% MeOH/10% water]

Example 1, Part H: 1-Methyl-4-methylamino-7-phenyl-triazolo[5,1-b]purine

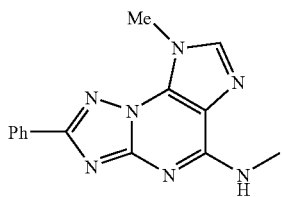

1

A mixture of 1G (13.2 mg, 0.0498 mmol), MeNH$_2$.HCl (20.6 mg, 0.149 mmol), Hunig's base (20.6 mg, 0.149 mmol), in n-butanol (2.0 mL) was heated under Microwave conditions at 150° C. for 30 min. On cooling, extractive EtOAc/H$_2$O workup followed by chromatography using Reverse-Phase PREP HPLC provided the title compound (9.1 mg, 60%) as a white solid. $^1$H NMR (d-MeOD, 400 MHz): 8.2 (m, 3H), 7.4 (m, 3H), 4.3 (s, 3H), 3.2(s, 3H); ESI m/z=279.31 [(M+H)$^+$; calcd for $C_{14}H_{11}N_5O+H$: 280]; HPLC RT=2.410 min [4 min grad, 10% MeOH/90% water to 90% MeOH/10% water]

EXAMPLE 2

1-Methyl-4-methylamino-7-(3'-bromophenyl)-triazolo[5,1-b]purine

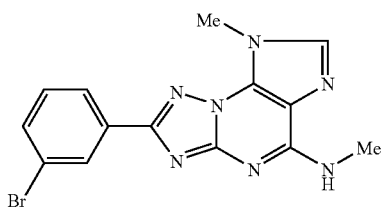

2

Example 2. Part A: 5-(3-Bromophenyl)-2H-[1,2,4]-triazol-3-ylamine

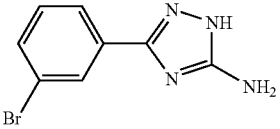

2A

Aminoguanidine.hydrochloride (4.12 g, 0.037 moles) was added to stirred solution of a 0.5M sodium methoxide solution in methanol (75 ml) cooled to 0° C. After stirring for 30 minutes, a solution of commercially available methyl-3-bromo-benzoate (3.22 g, 0.015 moles) in methanol (10 ml) was added dropwise. The reaction mixture was allowed to warm to room temperature then refluxed for 16 hours. The reaction mixture was poured into an ice/water mix, acidified to pH 3–4 with 3N HCl and filtered. The residue was washed with diethyl ether then dried to give the 2A as a white solid (1.55 g, 65%) $^1$H NMR (d-MeOD, 400 MHz): 8.10(s, 1H), 7.85 (d, 1H), 7.50 (d, 1H), 7.35 (d, 1H); ESI m/z=304.31 [(M+H)$^+$; calcd for $C_{14}H_{11}N_5O+H$: 305]; HPLC RT=1.807 min [4 min grad, 10% MeOH/90% water to 90% MeOH/10% water]

Example 2 Part B: 1-Methyl-4-methylamino-7-(3'-bromophenyl)-triazolo[5,1-b]purine 2 was prepared by condensing 1D with 2A in place of 5-amino-3-phenyltriazole, in a manner analogous to that described in Example 1, Part E. This condensation product was further elaborated as described in Example 1 to produce 2 as an off-white solid. $^1$H NMR (d-MeOD, 400 MHz): 8.40(m, 2H), 7.90 (s, 1H), 7.85 (m, 2H), 4.35 (s, 3H), 3.20 (s, 3H). ESI m/z=358.20 [(M+H)$^+$; calcd for $C_{14}H_{11}N_5O+H$: 359]; HPLC RT=3.330 min [4 min grad, 10% MeOH/90% water to 90% MeOH/10% water]

EXAMPLE 3

1-Methyl-4-methylamino-7-(3'-cyanophenyl)-triazolo[5,1-b]purine

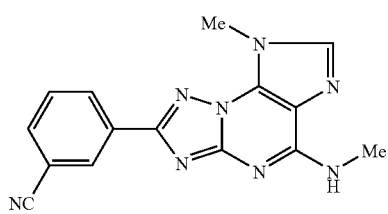

3

Example 3 Part A: 1-Methyl-4-methylamino-7-(3'-cyanophenyl)-triazolo[5,1-b]purine A mixture of 2 (15.568 g, 76.3 mmol), zinc cyanide (30 g, 91.6 mmol), tetrakistriphenylphosphine (30 g, 91.6 mmol) in DMF was heated at 120° C. for 10 min. under Microwave heating conditions. The reaction mixture was cooled to room temperature, diluted with ethyl acetate and filtered. The filtrate was concentrated in vacuo, and the residue purified by chromatography on Reverse-Phase PREP HPLC. The product was obtained as a white solid (17.02 g, 45%). $^1$H NMR (d-MeOD, 400 MHz): 8.55(m, 2H), 7.90 (s, 1H), 7.80

(m, 2H), 4.30 (s, 3H), 3.30 (s, 3H). ESI m/z=304.31 [(M+H)+; calcd for C$_{14}$H$_{11}$N$_5$O+H: 305]; HPLC RT=2.740 min[4 min grad, 10% MeOH/90% water to 90% MeOH/10% water]

EXAMPLE 4

1-Methyl-4-methylamino-7-methylthiotriazolo[5,1-b]purine

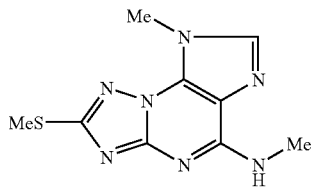

Example 4, Part A: 1-Methyl-2-methanesulfonyl-7-methylthio-4H-triazolo[5,1-b]purin-4-one

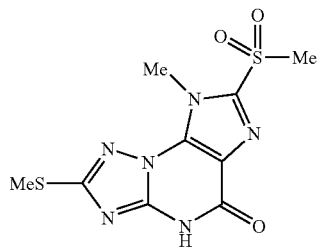

Commercially available 3-amino-5-melthylthio-1H-1,2,4-triazole (260 mg, 2.0 mmol), 1D (506 mg, 2.0 mmol) and cesium carbonate (650 mg, 2.0 mmol) were dissolved in DMF (25 mL) and sealed in a tube. The reaction mixture was heated for 48 h at 110° C., then allowed to cool to room temperature, and diluted with ethyl acetate (10 mL). The product was filtered and dried to obtain 628 mg (~100%) of the product as a tan solid. LCMS determined the product was greater than 96% pure M+H+=315.

Example 4, Part B: 1-Methyl-7-methylthio-4H-triazolo[5,1-b]purin-4-one

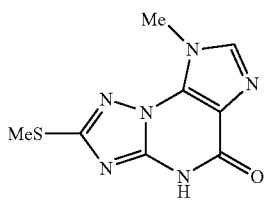

4A (628 mg, 2.0 mmol) was dissolved in 20 mL of anhydrous dioxane. A 1.0 molar solution of lithium triethylborohydride (5 mL, 5.0 mmol) was added over 15 min, and the reaction mixture stirred for 4 hours at room temperature. The reaction mixture was concentrated in vacuo, and purified by reverse-phase HPLC to produce 4B, 60 mg (13%) of 4B as a off-white solid. M+H+=237.

Example 4, Part C: 4-chloro-1-methyl-7-methylthio-1H-[1,2,4]triazolo[5,1-b]purine

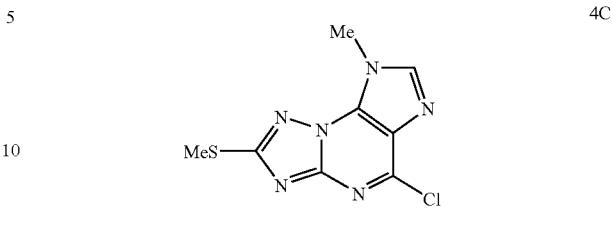

4B (55 mg, 0.23 mmol) was heated at 100° C. overnight in phosphorous oxychloride (10 mL). The reaction mixture was cooled to room temperature, and the excess reagent removed in vacuo to provide 60 mg (~100%) of 4C as a solid. M+H+=253, 255.

Example 4, Part D: 1-Methyl-4-methylamino-7-methylthiotriazolo[5,1-b]purine 4C (25 mg, 0.098 mmol), methylamine hydrochloride (25 mg, 0.3 mmol), and 0.5 mL of hunigs base were added to 2 mL of n-butanol, sealed in a microwave reaction vessel and heated at 150° C. for 30 min. The reaction mixture was concentrated and purified by reverse phase HPLC to yield the title compound 4, (5 mg) as a solid. M+H+=250.

UTILITY

The compounds and compositions of this invention are useful in treating conditions that are characterized by the activity of IKK, release of NF-κB, and/or enhanced levels of TNF-α. The term "treating" or "treatment" denotes prevention, partial alleviation, or cure of the disease or disorder or its symptoms or consequences. Inhibition or suppression of IKK, NF-κB and/or TNF-α may occur locally, for example, within certain tissues of the subject, or more extensively throughout the subject being treated for such a disease. Inhibition or suppression of IKK, NF-κB and/or TNF-α may occur by one or more mechanisms, e.g., by inhibiting or suppressing any step of the pathway(s). The term "NF-κB-associated condition" refers to diseases that are characterized by release of NF-κB from the cytoplasm (e.g., upon phosphorylation of IκB). The term "TNF-α-associated condition" is a condition characterized by enhanced levels of TNF-α. In the instant specification, the term "NF-κB-associated condition" will include a TNF-α-associated condition but is not limited thereto as NF-κB is involved in the activity and upregulation of other pro-inflammatory proteins and genes. The term "inflammatory or immune disease" is used herein to encompass IKK-associated conditions, NF-κB-associated conditions, and TNF-α-associated conditions, e.g., any condition, disease, or disorder that is associated with activity of IKK, NF-κB and/or enhanced levels of TNF-α.

The inventive compounds and compositions are useful for treating a variety of diseases including, but not limited to, treatment of transplant rejections (e.g., kidney, liver, heart, lung, pancreas, bone marrow, cornea, small bowel, skin allografts, skin homografts and heterografts, etc.) or tolerance to organ transplantion; rheumatoid arthritis, psoriatic arthritis, multiple sclerosis, inflammatory bowel disease (such as Crohn's disease and ulcerative colitus); antiviral and autoimmune diseases including herpes simplex type 1 (HSV-1), herpes simplex type 2 (HSV-2), cytomegalovirus, Epstein-Barr, human immunodeficiency virus (HIV), Addison's disease (autoimmune disease of the adrenal glands), idiopathic adrenal insufficiency, and autoimmune polyglandular disease (also known as autoimmune polyglandular syndrome); Alzheimer's, Parkinson's, and Creutzfeldt-Jacob diseases; septic shock; hematopoiesis; inflammatory diseases such as osteoarthritis, acute pancreatitis, and chronic pancreatitis; inflammatory disorders of the central nervous system, including HIV encephalitis, cerebral malaria, and meningitis, atherosclerosis, and ataxia telangiectasis; respiratory allergies including asthma, hayfever, and allergic rhinitis; chronic obstructive pulmonary disease; fungal infections such as mycosis fungoides; and psoriasis, glomerulonephritis, serum sickness, lupus (systematic lupus erythematosis), urticaria, scleraclerma, contact dermatitis, dermatomyositis, alopecia, atopic eczemas, and ichthyosis. The term "inflammatory or immune disease" as used herein includes all of the above-referenced diseases and disorders.

The inventive compounds are also effective in treating oncological diseases, in treating cancer and tumors, such as solid tumors, lymphomas and leukemia, and in particular, breast cancer, prostate cancer, and Hodgkin's lymphoma.

The present invention thus provides methods for treating such conditions, comprising administering to a subject in need thereof an effective amount of at least one compound of formula I or a salt thereof. Other therapeutic agents such as those described below may be employed in combination with compounds of formula I. In the methods of the present invention, such other therapeutic agent(s) may be administered prior to, simultaneously with, or following administration of the inventive compound(s).

The present invention also provides pharmaceutical compositions capable of treating IKK, NF-κB and/or TNF-α associated conditions, as described above. The inventive compositions may contain other therapeutic agents and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of formula I may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aqueous or non-aqueous solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The effective amount of a compound of the present invention may be determined by one of ordinary skill in the art, and includes exemplary dosage amounts for a mammal of from about 0.05 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like, subject to IKK, NF-κB and/or TNF-α associated conditions.

The inventive compounds and compositions may be employed alone or in combination with each other and/or other suitable therapeutic agents useful in treating IKK, NF-κB and/or TNF-α associated conditions. Exemplary of such other therapeutic agents include corticosteroids, rolipram, calphostin, CSAIDs, 4-substituted imidazo [1,2-A] quinoxalines as disclosed in U.S. Pat. No. 4,200,750; Interleukin-10, glucocorticoids, salicylates, nitric oxide, and other immunosuppressants; nuclear translocation inhibitors, such as deoxyspergualin (DSG); non-steroidal antiinflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, Prograf); cytotoxic drugs such as azathiprine and cyclophosphamide; TNF-α inhibitors such as tenidap, anti-TNF antibodies or soluble TNF receptor, and rapamycin (sirolimus or Rapamune) or derivatives thereof; and other cancer drugs and treatments, including radiation treatments and daunorubicin.

The above other therapeutic agents, when employed in combination with the compounds of the present invention, may be used, for example, in those amounts indicated in the Physicians' Desk Reference (PDR) or as otherwise determined by one of ordinary skill in the art.

The inventive compounds have been tested and have shown activity as inhibitors of IKK, IkB, NF-κB and/or TNF-α. For example, THP-1 (human monocytic cell line) obtained from ATCC was cultured in RPMI-1640 supplemented with 10% FBS, sodium pyruvate, HEPES, 5-mercaptoethanol, Penicillin/Streptomycin. To a 96-well plate containing THP-1 cells (1.4×10$^6$/mL, 2.5×10$^5$ cells/well) in 180 μL RPMI-1640 was added 10 μL of the test compound in 10% DMSO. Typically, test compound concentrations of 0.1–100 μM were used in the assay. After one hour at 37° C., 10 μL of 1000 ng/mL lipopolysaccharide (LPS from Salmonella typhosa, Sigma) was added to each well. After an additional 6 hours at 37° C., the supernatants were collected following a 5 minute centrifugation of the plate to pellet the cells. The amount of TNFα in these supernatants was then measured using a TNFα-specific ELISA (Pharmingen). After subtracting out the amount of TNFα in a control that had not been treated with LPS, the percent inhibition was calculated versus a control that was treated with LPS but with no test compound added. The compounds of this invention are active in vivo in the LPS-induced TNFα secretion model. Likewise, assays known in the field are applied to establish the activity of the compounds as inhibitors of IKK, IkB, and/or the NF-κB pathway.

We claim:
1. A compound of Formula (I),

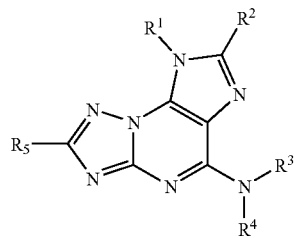

(I)

enantiomers, diastereomers, and salts, thereof wherein
$R^1$ is
(a) hydrogen, or
(b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^1$, $Z^2$ and $Z^3$;
(c) —OR$^{9a}$;
$R^2$ is
(a) hydrogen, halo, cyano,
(b) alkyl, alkenyl, alkynyl, haloalkyl, alkoxy, cycloalkoxy, heterocyclooxy, aryloxy, heteroaryloxy, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1a}$, $Z^{2a}$ and $Z^{3a}$; or
(c) —OR$^{9a}$, —SR$^{9a}$ or —SO$_2$R$^{9a}$
$R^3$ and $R^4$ are independently
(a) hydrogen,
(b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1b}$, $Z^{2b}$ and $Z^{3b}$;
(c) —OR$^{10}$, —NR$^{11}$R$^{12}$, —N(R$^{11}$)C(O)R$^{10}$, —N(R$^{11}$)C(O)OR$^{10}$, —N(R$^{11}$)SO$_2$R$^{13}$, or —C(O)NR$^{11}$R$^{12}$, —SO$_2$NR$^{11}$R$^{12}$, —N(R$^{11}$)C(O)NR$^{11a}$R$^{12}$, or —N(R$^{11}$)SO$_2$NR$^{11a}$R$^{12}$; or
(d) $R^3$ and $R^4$ together with the nitrogen atom to which they are attached combine to form a heterocyclo ring optionally independently substituted as valence allows with one or more $Z^{1b}$, $Z^{2b}$ and $Z^{3b}$;
$R^5$ is
(a) hydrogen, hydroxy, halo, or cyano,
(b) alkyl, alkenyl, alkynyl, cycloalkyl, heterocyclo, aryl, heteroaryl, (cycloalkyl)alkyl, (heterocyclo)alkyl, (aryl)alkyl, or (heteroaryl)alkyl any of which may be optionally independently substituted as valence allows with one or more $Z^{1d}$, $Z^{2d}$ and $Z^{3d}$; or
(c) —OR$^{6a}$, —SR$^{9a}$, SO$_2$R$^{9a}$, SO$_2$NR$^{7a}$R$^{8a}$, —NR$^{7a}$R$^{8a}$, —N(R$^{7a}$)SO$_2$R$^9$, —N(R$^{7a}$)SO$_2$NR$^{7b}$R$^{8b}$, —N(R$^{7a}$)C(O)R$^{6a}$, —N(R$^{7a}$)C(O)NR$^{7b}$R$^{8b}$, —N(R$^{7a}$)C(O)OR$^{6a}$, —C(O)R$^{6a}$, —C(O)OR$^{6a}$, —OC(O)R$^{6a}$, —C(O)NR$^{7a}$R$^{8a}$, or —OC(O)NR$^{7a}$R$^{8a}$;
$R^{6a}$ and $R^{6b}$ are independently
(a) hydrogen, or
(b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1c}$, $Z^{2c}$ and $Z^{3c}$;
$R^{7a}$, $R^{7b}$, $R^{8a}$ and $R^{8b}$ are independently
(a) hydrogen,
(b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1d}$, $Z^{2d}$ and $Z^{3d}$; or
(c) —OR$^{6b}$, —NR$^{7c}$R$^{8c}$, —N(R$^{7c}$)SO$_2$R$^{9b}$, —N(R$^{7c}$)C(O)R$^{6b}$, —N(R$^{7c}$)C(O)OR$^{6b}$, —SO$_2$NR$^{7c}$R$^{8c}$, —SO$_2$R$^{9b}$, —C(O)R$^{6b}$, —C(O)OR$^{6b}$, or —C(O)NR$^{7c}$R$^{8c}$;
(d) $R^{7a}$ and $R^{8a}$ together with the nitrogen atom to which they are attached combine to form a heterocyclo ring optionally independently substituted as valence allows with one or more $Z^{1d}$, $Z^{2d}$ and $Z^{3d}$;
$R^{7c}$ and $R^{8c}$ are independently
(a) hydrogen,
(b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1^d}$, $Z^{2^d}$ and $Z^{3^d}$;
  (c) $R^{7^e}$ and $R^{8^e}$ together with the nitrogen atom to which they are attached combine to form a heterocyclo ring optionally independently substituted as valence allows with one or more $Z^{1^d}$, $Z^{2^d}$ and $Z^{3^d}$;
$R^9$, $R^{9^a}$ and $R^{9^b}$ are independently alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1^d}$, $Z^{2^d}$ and $Z^{3^d}$;
$R^{10}$, $R^{11}$, $R^{11^a}$ and $R^{12}$ are independently
  (a) hydrogen, or
  (b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1^e}$, $Z^{2^e}$ and $Z^{3^e}$;
  (c) $R^{11}$ and $R^{12}$ together with the nitrogen atom to which they are attached combine to form a heterocyclo ring optionally independently substituted as valence allows with one or more $Z^{1^d}$, $Z^{2^d}$ and $Z^{3^d}$;
$R^{13}$ is alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1^e}$, $Z^{2^e}$ and $Z^{3^e}$;
$Z^{1\text{-}1^e}$, $Z^{2\text{-}2^e}$, and $Z^{3\text{-}3^e}$ are optional substituents at each occurrence independently selected from $W^{1-5}$ optionally substituted as valance allows with $V^{1-5}$; where $W^{1-5}$ are independently
  (1) a bond
  (2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl; or
where $V^{1-5}$ are independently
  (1) H
  (2) alkyl, haloalkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl;
  (3) —$U^1$—O—$Y^5$,
  (4) —$U^1$—S—$Y^5$,
  (5) —$U^1$—C(O)H, —$U^1$—C(O)$_t$—$Y^5$ where t is 1 or 2,
  (6) —$U^1$—SO$_3$—H, or —$U^1$—S(O)$_t$$Y^5$,
  (7) —$U^1$-halo,
  (8) —$U^1$-cyano,
  (9) —$U^1$-nitro,
  (10) —$U^1$—NY$^2$Y$^3$,
  (11) —$U^1$—N(Y$^4$)—C(O)—Y$^1$,
  (12) —$U^1$—N(Y$^4$)—C(S)—Y$^1$,
  (13) —$U^1$—N(Y$^4$)—C(O)—NY$^2$Y$^3$,
  (14) —$U^1$—N(Y$^4$)—C(S)—NY$^2$Y$^3$,
  (15) —$U^1$—N(Y$^4$)—C(O)O—Y$^5$,
  (16) —$U^1$—N(Y$^4$)—S(O)$_2$—Y$^1$,
  (17) —$U^1$—N(Y$^4$)—S(O)$_2$—NY$^2$Y$^3$,
  (18) —$U^1$—C(O)—NY$^2$Y$^3$,
  (19) —$U^1$—OC(O)—NY$^2$Y$^3$,
  (20) —$U^1$—S(O)$_2$—N(Y$^4$)—Y$^1$,
  (21) —$U^1$—N(Y$^4$)—C(=NV$^{1^a}$)—NY$^2$Y$^3$,
  (22) —$U^1$—N(Y$^4$)—C(=NV$^{1^a}$)—Y$^1$,
  (23) —$U^1$—C(=NV$^{1^a}$)—NY$^2$Y$^3$,
  (24) oxo;
  (25) —Y$^5$;
  (26) —$U^1$—C(O)—NY$^2$—OY$^5$, $V^{1^a}$ is independently hydrogen, alkyl, —CN, —C(O)Y$^1$, —S(O)$_2$Y$^5$, S(O)$_2$NY$^2$Y$^3$; Y$^1$, Y$^2$, Y$^3$, Y$^4$ and Y$^5$
  (1) are each independently hydrogen, alkyl, haloalkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl, or (heteroaryl)alkyl; or
  (2) Y$^2$ and Y$^3$ may together be alkylene or alkenylene, completing a 3- to 8-membered saturated or unsaturated ring together with the atoms to which they are attached, or
  (3) Y$^2$ or Y$^3$, together with Y$^1$, may be alkylene or alkenylene completing a 3- to 8-membered saturated or unsaturated ring together with the nitrogen atoms to which they are attached, or
  (4) Y$^2$ and Y$^3$ together with the nitrogen atom to which they are attached may combine to form a group —N=CY$^6$Y$^7$ where Y$^6$ and Y$^7$ are each independently H or alkyl; and
$U^1$ is independently
  (1) a single bond,
  (2) alkylene,
  (3) alkenylene,
  (4) alkynylene,
  (5) —$U^2$—O—$U^3$—,
  (6) —$U^2$—NY$^4$—$U^3$—,
  (7) —$U^2$—S—$U^3$—, or
  (8) —$U^2$—S(O)$_2$—$U^3$—,
$U^2$ is independently selected from
  (1) a single bond,
  (2) alkylene,
  (3) alkenylene,
  (4) alkynylene; and
$U^3$ is independently selected from
  (1) alkylene,
  (2) alkenylene,
  (3) alkynylene.

2. The compound of claim 1, wherein
$R^3$ and $R^4$ are independently
  (a) hydrogen,
  (b) alkyl, haloalkyl, (hydroxy)alkyl, cycloalkyl, (cycloalkyl)alkyl, (heterocyclo)alkyl, (aryl)alkyl or (heteroaryl)alkyl and of which may be optionally independently substituted as valence allows with one or more $Z^{1^b}$, $Z^{2^b}$ and $Z^{3^b}$; or
  (c) $R^3$ and $R^4$ together with the nitrogen atom to which they are attached combine to form a heterocyclo ring optionally independently substituted as valence allows with one or more $Z^{1^b}$, $Z^{2^b}$ and $Z^{3^b}$.

3. The compound of claim 2, wherein
$R^5$ is
  (a) alkyl, alkenyl, alkynyl, aryl or heterocyclo any of which may be optionally independently substituted as valence allows with one or more $Z^{1^d}$, $Z^{2^d}$ and $Z^{3^d}$; or
  (b) —OR$^{6^a}$, —SR$^{9^a}$, SO$_2$R$^{9^a}$, SO2NR$^{7^a}$R$^{8^a}$.

4. The compound of claim 3, wherein
$Z^{1^b}$, $Z^{2^b}$ and $Z^{3^b}$ are optional substituents independently selected from alkyl, —$U^1$—OH, —$U^1$—OY$^5$, —$U^1$—NY$^2$Y$^3$, —$U^1$—C(O)$_t$H, —$U^1$—C(O)$_t$Y$^5$, —$U^1$—C(O)—NY$^2$—OY$^5$, or —$U^1$—N(Y$^4$)—C(O)—NY$^2$Y$^3$, —$U^1$—N(Y$^4$)—C(O)—Y$^1$, —$U^1$—N(Y$^4$)—C(O)O—Y$^5$, —$U^1$—C(O)—NY$^2$Y$^3$, —$U^1$—OC(O)—NY$^2$Y$^3$;
$Z^{1^e}$ is
  (a) —OH, —OY$^5$ or
  (b) aryl-V$^3$, wherein V$^3$ is H, —OH or —OY$^5$; $Z^{1^d}$, $Z^{2^d}$ and $Z^{3^d}$ are optional substituents independently selected from; (a) cyano, halo, —$U^1$—OH, —$U^1$—$OY^5$, —$U^1$—$NY^2Y^3$, —$U^1$—C(O)$_t$H, —$U^1$—C(O)$_t Y^5$, —$U^1$—S(O)$_t Y^1$, —$U^1$—C(O)—$NY^2$—$OY^5$, or —$U^1$—N($Y^4$)—C(O)—$NY^2Y^3$, —$U^1$—N($Y^4$)—C(O)—$Y^1$, —$U^1$—N($Y^4$)—C(O)O—$Y^5$, —$U^1$—C(O)—$NY^2Y^3$, —$U^1$—N($Y^4$)—S(O)$_2$—$Y^1$, —$U^1$—OC(O)—$NY^2Y^3$;

(b) alkyl optionally substituted with one or more cyano, halo, —$U^1$—OH, —$U^1$—$OY^5$, —$U^1$—$NY^2Y^3$, —$U^1$—C(O)$_t$H, —$U^1$—C(O)$_t Y^5$, —$U^1$—S(O)$_t Y^1$, —$U^1$—N($Y^4$)—C(O)—$Y^1$, —$U^1$—N($Y^4$)—C(O)O—$Y^5$, —$U^1$—C(O)—$NY^2Y^3$, —$U^1$—OC(O)—$NY^2Y^3$.

5. The compound of claim 4, wherein $R^3$ is hydrogen;

$R^4$ is alkyl, haloalkyl, (hydroxy)alkyl, cycloalkyl, (cycloalkyl)alkyl, (heterocyclo)alkyl, (aryl)alkyl or (heteroaryl)alkyl and of which may be optionally independently substituted as valence allows with one or more $Z^{1^b}$, $Z^{2^b}$ and $Z^{3^b}$;

$R^5$ is (a) alkynyl optionally substituted with $Z^{1^d}$ where $Z^{1^d}$ is aryl which may be further optionally independently substituted with one or more cyano, halo, —$U^1$—OH, —$U^1$—$OY^5$, —$U^1$—$NY^2Y^3$, —$U^1$—C(O)$_t$H, —$U^1$—C(O)$_t Y^5$, —$U^1$—S(O)$_t Y^1$, —$U^1$—N($Y^4$)—$U^3$—$NY^2Y^3$, —$U^1$—N($Y^4$)—$U^3$—$Y^5$, or —N($Y^4$)—$U^3$—H;

(b) aryl optionally independently substituted as valence allows with one or more $Z^{1^d}$, $Z^{2^d}$ and $Z^{3^d}$; or (c) —$OR^{6^a}$, —$SR^{9^a}$, $SO_2R^{9^a}$, $SO2NR^{7^a}R^{8^a}$;

$Z^{1^b}$, $Z^{2^b}$ and $Z^{3^b}$ are optional substituents independently selected from —$U^1$—OH, —$U^1$—$OY^5$, —$U^1$—$NY^2Y^3$, —C(O)$_t$H, —C(O)$_t Y^5$, —$U^1$—C(O)—$NY^2$—$OY^5$, —N($Y^4$)—C(O)—$Y^1$, N($Y^4$)—C(O)O—$Y^5$, —C(O)—$NY^2Y^3$, —OC(O)—$NY^2Y^3$;

$Z^{1^c}$ is (a) —$OY^5$ where $Y^5$ is aryl, or (b) aryl-$V^3$, wherein $V^3$ is —OH or —$OY^5$ where $Y^5$ is alkyl;

$Z^{1^d}$, $Z^{2^d}$ and $Z^{3^d}$ are optional substituents independently selected from (a) cyano, halo, —$U^1$—OH, —$U^1$—$OY^5$, —$U^1$—C(O)$_t$H, —$U^1$—C(O)$_t Y^5$, —S(O)$_t Y^1$, or (b) alkyl optionally substituted with one or more cyano, halo, —OH, —$OY^5$, $NY^2Y^3$, —C(O)—$NY^2Y^3$, —C(O)—$NY^2$—$OY^5$, —N($Y^4$)—C(O)—$Y^1$, —N($Y^4$)—C(O)O—$Y^5$, —N($Y^4$)—S(O)$_2$—$Y^1$, —C(O)$_t$H, —C(O)$_t Y^5$, —S(O)$_t Y^1$, —N($Y^4$)—$U^2$—Y, or —N($Y^4$)—$U^2$—H, where $U^1$ is a bond, alkylenyl or —O—$U^3$—.

6. The compound of claim 5, wherein $R^1$ is alkyl; and $R^2$ is hydrogen.

7. The compound of claim 6, wherein $R^5$ is (a) phenyl, pyridyl, pyrimidinyl, or acetyleneyl, any of which may be optionally independently substituted as valence allows with one or more $Z^{1^d}$, $Z^{2^d}$ and $Z^{3^d}$; or (b) —$OR^{6^a}$, —$SR^{9^a}$, $SO_2R^{9^a}$, $SO2NR^{7^a}R^{8^a}$;

$R^{6^a}$ is alkyl substituted with which may be optionally independently substituted as valence allows with $Z^{1^c}$, $Z^{2^c}$ and $Z^{3^c}$;

$Z^{1^c}$ is (a) —OH, —$OY^5$ or (b) aryl-$V^3$, wherein $V^3$ is H, —OH or —$OY^5$;

$Y^5$ is alkyl.

8. The compound of claim 7, wherein $Z^{1^d}$, $Z^{2^d}$ and $Z^{3^d}$ are optional substituents independently selected from;

cyano, halo, —$U^1$—OH, —$U^1$—$OY^5$, —$U^1$—$NY^2Y^3$, —$U^1$—C(O)$_t$H, —$U^1$—C(O)$_t Y^5$, —$U^1$—S(O)$_t Y^1$, —$U^1$—C(O)—$NY^2$—$OY^5$, or —$U^1$—N($Y^4$)—C(O)—$NY^2Y^3$, —$U^1$—N($Y^4$)—C(O)—$Y^1$, —$U^1$—N($Y^4$)—C(O)O—$Y^5$, —$U^1$—C(O)—$NY^2Y^3$, —$U^1$—N($Y^4$)—S(O)$_2$—$Y^1$, —$U^1$—OC(O)—$NY^2Y^3$;

wherein $U^1$ is a bond, alkylenyl or —O—$U^3$— and $Y^1$, $Y^2$, $Y^3$, $Y^4$, and $Y^5$ are independently selected from H or alkyl or haloalkyl.

9. A pharmaceutical composition comprising (a) at least one compound according to claim 1, or a pharmaceutically acceptable salt thereof, and (b) a pharmaceutically-acceptable carrier or diluent.

10. A method of treating an inflammatory or immune disease in which the inflammatory or immune disease is selected from rheumatoid arthritis, asthma, inflammatory bowel disease, chronic obstructive pulmonary disease, and psoriasis.

* * * * *